United States Patent [19]
Stolle et al.

[11] Patent Number: 6,069,160
[45] Date of Patent: *May 30, 2000

[54] HETEROATOM-CONTAINING BENZOCYCLOPENTANE-OXAZOLIDINONES

[75] Inventors: Andreas Stolle; Dieter Häbich, both of Wuppertal; Stephan Bartel, Bergisch Gladbach; Bernd Riedl; Martin Ruppelt, both of Wuppertal, all of Germany; Hanno Wild, Orange, Conn.; Rainer Endermann, Wuppertal, Germany; Klaus-Dieter Bremm, Recklinghausen, Germany; Hein-Peter Kroll, Wuppertal, Germany; Harald Labischinski, Wuppertal, Germany; Klaus Schaller, Wuppertal, Germany; Hans-Otto Werling, Wuppertal, Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/631,516

[22] Filed: Apr. 12, 1996

[30] Foreign Application Priority Data

Apr. 21, 1995 [DE] Germany ............................ 195 14 769
Nov. 27, 1995 [DE] Germany ............................ 195 44 106

[51] Int. Cl.$^7$ ...................... A61K 31/428; A61K 31/423; C07D 263/54; C07D 277/62
[52] U.S. Cl. ........................... 514/367; 514/375; 548/165; 548/221
[58] Field of Search ...................................... 548/165, 221; 514/367, 375

[56] References Cited

U.S. PATENT DOCUMENTS

| 4,705,799 | 11/1987 | Gregory | 514/376 |
|---|---|---|---|
| 4,801,600 | 1/1989 | Wang et al. | 514/376 |
| 4,921,869 | 5/1990 | Wang et al. | 514/376 |
| 4,965,268 | 10/1990 | Wang et al. | 514/253 |
| 4,970,217 | 11/1990 | Prucher et al. | 514/327 |
| 5,254,577 | 10/1993 | Carlson et al. | 514/376 |
| 5,475,014 | 12/1995 | Akasaka et al. | 514/367 |
| 5,529,998 | 6/1996 | Habich et al. | 514/367 |

FOREIGN PATENT DOCUMENTS

| 0311090 | 4/1989 | European Pat. Off. . |
|---|---|---|
| 0312000 | 4/1989 | European Pat. Off. . |
| 0609441 | 8/1994 | European Pat. Off. . |
| 0609905 | 8/1994 | European Pat. Off. . |

OTHER PUBLICATIONS

S. Abdelaal et al., J. Hetercyclic Chem., vol. 29, pp. 1069–1076 (1992).

C. Park et al., J. Chem. Soc., vol. 35, pp 1156–1163 (1992).

*Primary Examiner*—Mukund J. Shah
*Assistant Examiner*—Brenda Coleman
*Attorney, Agent, or Firm*—Norris, McLaughlin & Marcus, P.A.

[57] ABSTRACT

The invention relates to heteroatom-containing benzocyclopentaneoxazolidinones, to processes for their preparation and their use as medicaments, especially as antibacterial medicaments.

8 Claims, No Drawings

HETEROATOM-CONTAINING BENZOCYCLOPENTANE-OXAZOLIDINONES

The present invention relates to heteroatom-containing benzocyclopentaneoxazolidinones, to processes for their preparation and to their use as medicaments, in particular as antibacterial medicaments.

The publications U.S. Pat. Nos. 5,254,577, 4,705,799, EP 311 090, U.S. Pat. Nos. 4,801,600, 4,921,869, 4,965,268, EP 312 000 and C. H. Park et al., J. Med. Chem. 35, 1156 (1992) disclose N-aryloxazolidinones having an antibacterial action. Moreover, EP 609 905 Al discloses 3-(nitrogen-substituted) phenyl-5-beta-amidomethyloxazolidin-2-ones.

In addition, PCT 93 08 179 A describes oxazolidinone derivatives which act as monoamine oxidase inhibitors.

The present invention relates to heteroatom-containing benzocyclopentaneoxazolidinones of the general formula (I)

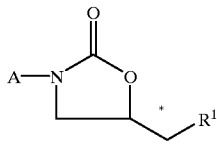

(I)

in which
  $R^1$ represents azido, hydroxyl or represents a group of the formula $—OR^2$, $O—SO_2R^3$ or $—NR^4R^5$, in which
    $R^2$ denotes straight-chain or branched acyl having up to 8 carbon atoms, or a hydroxy-protecting group,
    $R^3$ denotes straight-chain or branched alkyl having up to 4 carbon atoms or phenyl which is optionally substituted by straight-chain or branched alkyl having up to 4 carbon atoms,
    $R^4$ and $R^5$ are identical or different and denote cycloalkyl having 3 to 6 carbon atoms, hydrogen, phenyl or straight-chain or branched alkyl or alkoxy having in each case up to 8 carbon atoms, or an amino-protecting group, or
  $R^4$ or $R^5$ denotes a group of the formula $—CO—R^6$, $P(O)(OR^7)(OR^8)$ or $—SO^2—R^9$, in which
    $R^6$ denotes cycloalkyl or halogen substituted cycloalkyl each having 3 to 6 carbon atoms, trifluoromethyl, straight-chain or branched alkoxy having up to 8 carbon atoms, phenyl, benzyloxy or hydrogen, or
    $R^6$ denotes straight-chain or branched alkyl or alkenyl each having up to 8 carbon atoms which are optionally substituted by cyano, halogen or trifluoromethyl, or
    denotes straight-chain or branched thioalkyl or acyl having in each case up to 6 carbon atoms, or
    denotes a group of the formula $—NR^{10}R^{11}$, in which
      $R^{10}$ and $R^{11}$ are identical or different and denote hydrogen, phenyl or straight-chain or branched alkyl having up to 6 carbon atoms, or
    $R^6$ denotes a 5-membered aromatic heterocycle having up to 3 heteroatoms from the series S, N and/or O, which is optionally substituted by straight-chain or branched alkyl having up to 3 carbon atoms,
    $R^7$ and $R^8$ are identical or different and denote hydrogen or straight-chain or branched alkyl having up to 4 carbon atoms,
    $R^9$ denotes straight-chain or branched alkyl having up to 4 carbon atoms, or phenyl, A represents a radical of the formula

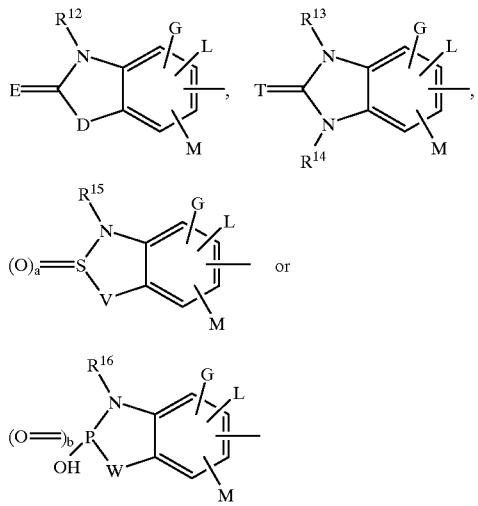

in which
  G, L and M are identical or different and represent hydrogen, carboxyl, halogen, cyano, formyl, trifluoromethyl, nitro, represent straight-chain or branched alkyl having up to 6 carbon atoms, or represent a group of the formula $—CO—NR^{17}R^{18}$, in which
    $R^{17}$ and $R^{18}$ are identical or different and denote hydrogen, straight-chain or branched alkyl having up to 4 carbon atoms, or phenyl,
  $R^{12}$ denotes hydrogen, cycloalkylcarbonyl or cycloalkyl having in each case 3 to 6 carbon atoms, or straight-chain or branched alkoxycarbonyl having up to 6 carbon atoms, or denotes straight-chain or branched alkyl or alkenyl having in each case up to 10 carbon atoms, which are optionally substituted by cyano, azido, trifluoromethyl, pyridyl, halogen, hydroxyl, carboxyl, straight-chain or branched alkoxycarbonyl having up to 6 carbon atoms, benzyloxycarbonyl, aryl having 6 to 10 carbon atoms, cycloalkyl having 3 to 6 carbon atoms and/or by a group of the formula $—(CO)_c—NR^{19}R^{20}$, $R^{21}—N—SO_2—R^{22}$, $R^{23}R^{24}—N—SO_2—$, $R^{25}—S(O)_d—$, or 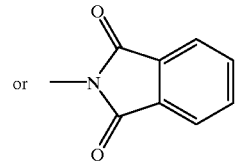

in which
  c is a number 0 or 1,
  $R^{19}$, $R^{20}$ and $R^{21}$ have the meaning given above of $R^{17}$ and $R^{18}$ and are identical to or different from it, or together with the nitrogen atom form a 5- to 6-membered, saturated heterocycle having optionally a further heteroatom from the series N, S and/or O, which can in turn optionally be substituted, even on a further nitrogen atom, by straight-chain or branched alkyl or acyl having up to 3 carbon atoms,
  $R^{23}$ and $R^{24}$ have the meaning given above of $R^{17}$ and $R^{18}$ and are identical to or different from it, d denotes a number 0, 1 or 2, $R^{22}$ and $R^{25}$ are identical or different and denote straight-chain or branched alkyl having up to 4 carbon atoms, benzyl, phenyl or tolyl, or $R^{12}$ denotes a residue of a formula

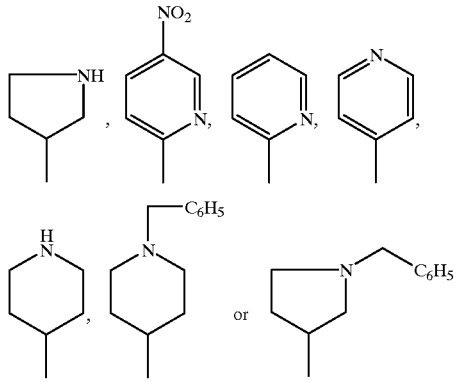

or denotes a group of the formula —COCCl$_3$ or straight-chain or branched acyl having up to 6 carbon atoms which is optionally substituted by trifluoromethyl, trichloromethyl or by a group of the formula —OR$^{26}$, in which $R^{26}$ denotes hydrogen or straight-chain or branched alkyl having up to 6 carbon atoms which is optionally substituted by aryl having up to 10 carbon atoms, or $R^{12}$ denotes a group of the formula —(CO)$_e$—NR$^{27}$R$^{28}$, —NR$^{29}$—SO$_2$R$^{30}$, R$^{31}$R$^{32}$—N—SO$_2$— or R$^{33}$—S(O)$_f$—, in which e has the meaning given above of c and is identical to or different from it, $R^{27}$ and $R^{28}$ and $R^{29}$ each have the meaning given above of $R^{19}$, $R^{20}$ and $R^{21}$ and are identical to or different from it, $R^{31}$ and $R^{32}$ have the meaning given above of $R^{17}$ and $R^{18}$ and are identical to or different from it, f has the meaning given above of d and is identical to or different from it, $R^{30}$ and $R^{33}$ have the meanings in each case given above of $R^{22}$ and $R^{25}$ and are identical to or different from these, D denotes an oxygen atom or sulphur atom, E denotes an oxygen or sulphur atom or a group of the formula NH, T denotes an oxygen atom or the NH group, $R^{13}$ and $R^{14}$ have the meaning given above of $R^{12}$ and are identical to or different from it, or T denotes a sulphur atom, with the proviso that $R^{13}$ and $R^{14}$ have the meaning given above of $R^{12}$ but do not represent hydrogen, or in the case where $R^{12}$, $R^{13}$ and $R^{14}$ do not represent hydrogen, E and/or T denote a group of the formula NR$^{34}$ in which R$^{34}$ with the exception of hydrogen has the meaning given above of $R^{12}$ and is identical to or different from it, or $R^{34}$ denotes cyano or a group of the formula —CO$_2$R$^{35}$, in which $R^{35}$ denotes benzyl or phenyl which are optionally substituted by nitro or halogen, V and W have the meaning given above of D or denote the abovementioned group N—R$^{14}$ and are identical to or different from it, a denotes a number 1 or 2, b denotes a number 0 or 1, $R^{15}$ and $R^{16}$ have the meaning given above of $R^{12}$ and are identical to or different from it, and the tautomeric forms and salts thereof.

Tautomerism in the compounds according to the invention refers, as a function of the above-listed substituent definitions of E, T, $R^{12}$, $R^{13}$ and $R^{14}$, to the possibility of displacement of the exocyclic double bonds into the 5-membered heterocycle.

Physiologically tolerated salts of the heteroatom-containing benzocyclopentaneoxazolidinones can be salts of the substances according to the invention with mineral acids, carboxylic acids or sulphonic acids. Particularly preferred examples are salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts which can be mentioned are salts with customary bases, such as, for example, alkali metal salts, (e.g. sodium or potassium salts), alkaline earth metal salts (e.g. calcium or magnesium salts) or ammonium salts, derived from ammonia or from organic amines such as, for example, diethylamine, triethylamine, ethyldiisopropylamine, procaine, dibenzylamine, N-methylmorpholine, dihydroabietylamine, 1-ephenamine or methyl-piperidine.

Other compounds which can function as salts are reaction products with $C_1$–$C_4$-alkyl halides, especially $C_1$–$C_4$-alkyl iodides.

Heterocycle generally represents a 5- to 6-membered, saturated or unsaturated ring which can contain as heteroatoms up to 3 oxygen, sulphur and/or nitrogen atoms. Preferred heterocycles are: thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl or piperazinyl.

Also included here are 5- to 6-membered saturated heterocycles attached via N which can additionally contain as heteroatoms up to 2 oxygen, sulphur and/or nitrogen atoms, such as, for example, piperidyl, morpholinyl or piperazinyl or pyrrolidinyl. Particular preference is given to piperidyl, morpholinyl and pyrrolidinyl.

Hydroxy-protecting group in the context of the definition given above generally represents a protecting group from the series: trimethylsilyl, triisopropylsilyl, tert-butyldimethylsilyl, benzyl, benzyloxycarbonyl, 2-nitrobenzyl, 4-nitrobenzyl, tert-butyloxycarbonyl, allyloxycarbonyl, 4-methoxybenzyl, 4-methoxybenzyloxycarbonyl, tetrahydropyranyl, formyl, acetyl, trichloroacetyl, 2,2,2-trichloroethoxycarbonyl, methoxyethoxymethyl, [2-(trimethylsilyl)ethoxy]methyl, benzoyl, 4-methylbenzoyl, 4-nitrobenzoyl, 4-fluorobenzoyl, 4-chlorobenzoyl or 4-methoxybenzoyl. Preference is given to acetyl, tert-butyldimethylsilyl or tetrahydropyranyl.

Amino-protecting groups in the context of the invention are the customary amino-protecting groups used in peptide chemistry.

These groups include preferably: benzyloxycarbonyl, 2,4-dimethoxybenzyloxycarbonyl, 4-methoxybenzyloxycarbonyl, methoxycarbonyl, ethoxycarbonyl, tert-butoxycarbonyl, allyloxycarbonyl, phthaloyl, 2,2,2-trichloroethoxycarbonyl, fluorenyl-9-methoxycarbonyl, formyl, acetyl, 2-chloroacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl, 4-nitrophenyl, 4-methoxyphenyl or triphenylmethyl.

The compounds according to the invention can exist in stereoisomeric forms whose relationship to one another is either that of image to mirror image (enantiomers) or not (diastereomers). The invention relates both to the enantiomers or diastereomers or their respective mixtures. The racemic forms, like the diastereomers, can be separated into the stereoisomerically uniform constituents in a known manner.

Preferred compounds of the general formula (I) are those in which $R^1$ represents azido, hydroxyl or represents a group of the formula —$OR^2$, —O—$SO_2R^3$ or —$NR^4R^5$, in which
  $R^2$ denotes straight-chain or branched acyl having up to 6 carbon atoms, or benzyl,
  $R^3$ denotes straight-chain or branched alkyl having up to 3 carbon atoms, phenyl or tolyl,
  $R^4$ and $R^5$ are identical or different and denote cyclopropyl, cyclobutyl, cyclopentyl, cyclohexyl, hydrogen, phenyl or straight-chain or branched alkyl or alkoxy having in each case up to 6 carbon atoms, tert-butoxycarbonyl or benzyloxycarbonyl, or
  $R^4$ or $R^5$ denotes a group of the formula —CO—$R^6$, —P(O)($OR^7$)($OR^8$) or —$SO_2$—$R^9$, in which
    $R^6$ denotes cyclopropyl, fluorine substituted cyclopropyl, cyclobutyl, cyclopentyl, cyclohexyl, trifluoromethyl or straight-chain or branched alkoxy having up to 6 carbon atoms, phenyl, benzyloxy or hydrogen, or
    $R^6$ denotes straight-chain or branched alkyl or alkenyl each having up to 6 carbon atoms which are optionally substituted by cyano, fluorine, chlorine, bromine or trifluoromethyl, or
    denotes straight-chain or branched thioalkyl or acyl having in each case up to 5 carbon atoms, or
    denotes a group of the formula —$NR^{10}R^{11}$, in which
      $R^{10}$ and $R^{11}$ are identical or different and denote hydrogen, phenyl or straight-chain or branched alkyl having up to 4 carbon atoms, or
    $R^6$ denotes isoxazolyl, furyl, thienyl, pyrroyl, oxazolyl or imidazolyl which are optionally substituted by methyl,
    $R^7$ and $R^8$ are identical or different and denote hydrogen or straight-chain or branched alkyl having up to 3 carbon atoms,
    $R^9$ denotes straight-chain or branched alkyl having up to 3 carbon atoms, or phenyl,
A represents a radical of the formula

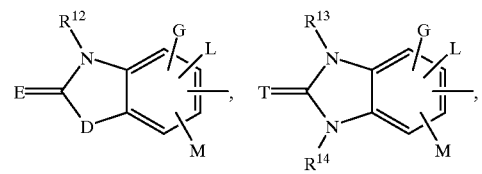

-continued

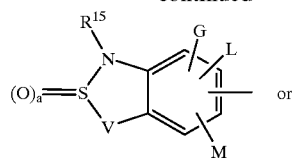

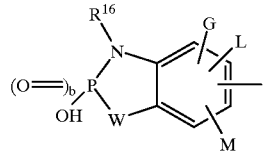

in which
  G, L and M are identical or different and represent hydrogen, carboxyl, fluorine, chlorine, bromine, iodine, cyano, trifluoromethyl, formyl, nitro, represent straight-chain or branched alkyl having up to 4 carbon atoms, or represent a group of the formula —CO—$NR^{17}R^{18}$, in which
    $R^{17}$ and $R^{18}$ are identical or different and denote hydrogen, straight-chain or branched alkyl having up to 3 carbon atoms, or phenyl,
  $R^{12}$ denotes hydrogen, cyclopropylcarbonyl, cyclopropyl, cyclobutyl, cyclopentyl, cyclohexyl, or
  straight-chain or branched alkoxycarbonyl having up to 4 carbon atoms, or
  straight-chain or branched alkyl or alkenyl having in each case up to 9 carbon atoms which are optionally substituted by cyano, azido, trifluoromethyl, pyridyl, fluorine, chlorine, bromine, hydroxyl, phenyl, carboxyl, straight-chain or branched alkoxycarbonyl having up to 5 carbon atoms, benzyloxycarbonyl, naphthyl, cyclopropyl, cyclopentyl, cyclohexyl and/or by a group of the formula —(CO)$_c$—$NR^{19}R^{20}$, $R^{21}$—N—$SO_2$—$R^{22}$, $R^{23}R^{24}$—N—$SO_2$—, $R^{25}$—S(O)$_d$—, or

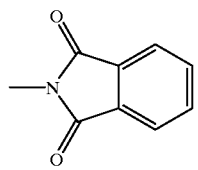

in which
  c denotes a number 0 or 1,
  $R^{19}$, $R^{20}$ and $R^{21}$ have the meaning given above of $R^{17}$ and $R^{18}$ and are identical to or different from it, or together with the nitrogen atom form a morpholinyl, pyrrolidinyl, piperazinyl or piperidyl ring which are optionally substituted, even via the free N function, by methyl, ethyl or acetyl,
  $R^{23}$ and $R^{24}$ have the meaning given above of $R^{17}$ and $R^{18}$ and are identical to or different from it,
  d denotes a number 0, 1 or 2,
  $R^{22}$ and $R^{25}$ are identical or different and denote straight-chain or branched alkyl having up to 3 carbon atoms, benzyl, phenyl or tolyl, or $R^{12}$ denotes a residue of a formula

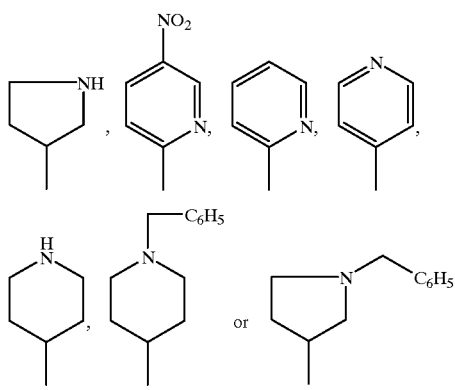

or denotes a group of the formula —COCCl$_3$ or straight-chain or branched acyl having up to 5 carbon atoms which is optionally substituted by trifluoromethyl, trichloromethyl or a group of the formula —OR$^{26}$, in which $R^{26}$ denotes hydrogen or straight-chain or branched alkyl having up to 5 carbon atoms which is optionally substituted by phenyl or naphthyl, or $R^{12}$ denotes a group of the formula —(CO)$_e$—NR$^{27}$R$^{28}$, —NR$^{29}$—SO$_2$R$^{30}$, R$_{31}$R$_{32}$—N—SO$_2$— or R$^{33}$—S(O)$_f$—, in which e has the meaning given above of c and is identical to or different from it, $R^{27}$, $R^{28}$ and $R^{29}$ have the meaning in each case given above of $R^{19}$, $R^{20}$ and $R^{21}$ and are identical to or different from it, $R^{31}$ and $R^{32}$ have the meaning given above of $R^{17}$ and $R^{18}$ and are identical to or different from it, f has the meaning given above of d and is identical to or different from it, $R^{30}$ and $R^{33}$ have the meanings in each case given above of $R^{22}$ and $R^{25}$ and are identical to or different from these, D denotes an oxygen or sulphur atom, E denotes an oxygen or sulphur atom or a group of the formula NH, T denotes an oxygen atom or the NH group, $R^{13}$ and $R^{14}$ have the meaning given above of $R^{12}$ and are identical to or different from it, or T denotes a sulphur atom, with the proviso that $R^{13}$ and $R^{14}$ have the meaning given above of $R^{12}$ but do not represent hydrogen, or, in the case where $R_{12}$, $R^{13}$ and $R^{14}$ do not represent hydrogen, E and/or T denote a group of the formula NR$^{34}$ in which R$^{34}$ with the exception of hydrogen has the meaning given above of $R^{12}$ and is identical to or different from it, or $R^{34}$ denotes cyano or a group of the formula —CO$_2$R$^{35}$, in which $R^{35}$ denotes benzyl or phenyl which are optionally substituted by nitro, fluorine, chlorine or bromine, V and W have the meaning given above of D or denote the abovementioned group N—R$^{14}$ and are identical to or different from it, a denotes a number 1 or 2, b denotes a number 0 or 1, $R^{15}$ and $R^{16}$ have the meaning given above of $R^{12}$ and are identical to or different from it, and the tautomeric forms and salts thereof.

Particularly preferred compounds of the general formula (I) are those in which $R^1$ represents azido, hydroxyl or represents a group of the formula —OR$^2$, —O—SO$_2$R$^3$ or —NR$^4$R$^5$, in which $R^2$ denotes straight-chain or branched acyl having up to 5 carbon atoms, or benzyl, $R^3$ denotes methyl, ethyl, phenyl or tolyl, $R^4$ and $R^5$ are identical or different and denote cyclopropyl, cyclobutyl, cyclopentyl, cyclohexyl, hydrogen, phenyl or straight-chain or branched alkyl or alkoxy having in each case up to 5 carbon atoms, tert-butoxycarbonyl or benzyloxycarbonyl, or $R^4$ or $R^5$ denotes a group of the formula —CO—R$^6$, —P(O)(OR$^7$)(OR$^8$) or —SO$_2$—R$^9$, in which $R^6$ denotes cyclopropyl, fluorine substituted cyclopropyl, cyclobutyl, cyclopentyl, cyclohexyl, trifluoromethyl or straight-chain or branched alkoxy having up to 5 carbon atoms, phenyl, benzyloxy or hydrogen, $R^6$ denotes straight-chain or branched alkyl or alkenyl each having up to 5 carbon atoms which are optionally substituted by cyano, fluorine, chlorine, bromine or trifluoromethyl, or denotes straight-chain or branched thioalkyl or acyl having in each case up to 4 carbon atoms, or denotes a group of the formula —NR$^{10}$R$^{11}$ in which $R^{10}$ and $R^{11}$ are identical or different and denote hydrogen, phenyl or straight-chain or branched alkyl having up to 3 carbon atoms, or $R^6$ denotes isoxazolyl, furyl, oxazolyl or imidazolyl which are optionally substituted by methyl, $R^7$ and $R^8$ are identical or different and denote hydrogen, methyl or ethyl, $R^9$ denotes methyl or phenyl, A represents a radical of the formula

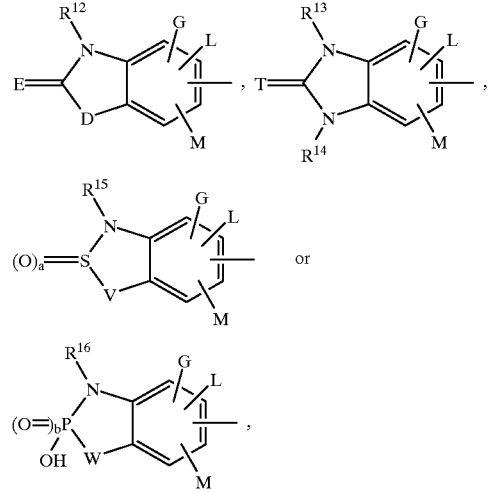

in which

G, L and M are identical or different and represent hydrogen, carboxyl, fluorine, chlorine, bromine, iodine, cyano, formyl, nitro, represent straight-chain or branched alkyl having up to 3 carbon atoms or represent a group —CO—NH$_2$, $R^{12}$ denotes hydrogen, cyclopropylcarbonyl, cyclopropyl, cyclobutyl, cyclopentyl, cyclohexyl, or straight-chain or branched alkoxycarbonyl having up to 3 carbon atoms, or straight-chain or branched alkyl or alkenyl having in each case up to 8 carbon atoms which are optionally substituted by cyano, azido, trifluoromethyl, pyridyl, fluorine, chlorine, bromine, phenyl, hydroxyl, carboxyl, straight-chain or branched alkoxycarbonyl having up to 4 carbon atoms, benzyloxycarbonyl, cyclopropyl, cyclopentyl, cyclohexyl and/or by a group of the formula —(CO)$_c$—NR$^{19}$R$^{20}$, R$^{21}$—N—SO$_2$—R$^{22}$, R$^{23}$R$^{24}$—N—SO$_2$—, R$^{25}$—S(O)$_d$— or

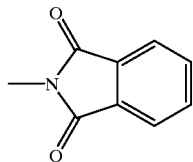

in which
c denotes a number 0 or 1,
R$^{19}$, R$^{20}$, R$^{21}$, R$^{23}$ and R$^{24}$ are identical or different and denote hydrogen, methyl or ethyl,
d denotes a number 0, 1 or 2,
R$^{22}$ and R$^{25}$ are identical or different and denote straight-chain or branched alkyl having up to 4 carbon atoms, benzyl, phenyl or tolyl, or
R$^{12}$ denotes a residue of a formula

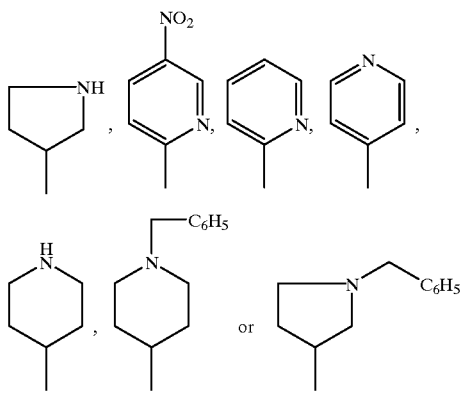

or denotes a group of the formula —COCCl$_3$ or straight-chain or branched acyl having up to 4 carbon atoms which is optionally substituted by trifluoromethyl, trichloromethyl, a group of the formula —OR$^{26}$, in which
R$^{26}$ denotes hydrogen or straight-chain or branched alkyl having up to 4 carbon atoms which is optionally substituted by phenyl, or
R$^{12}$ denotes a group of the formula —(CO)$_e$—NR$^{27}$R$^{28}$ or R$^{33}$—S(O)$_f$—, in which
e denotes the number 1,
R$^{27}$ and R$^{28}$ are identical or different and denote hydrogen, methyl or ethyl,
f has the meaning given above of d and is identical to or different from it,
R$^{33}$ denotes methyl, phenyl, tolyl or benzyl,
D denotes an oxygen or sulphur atom,
E denotes an oxygen or sulphur atom or a group of the formula NH,
T denotes an oxygen atom or the NH group, R$^{13}$ and R$^{14}$ have the meaning given above of R$^{12}$ and are identical to or different from it, or
T denotes a sulphur atom,
with the proviso that R$^{13}$ and R$^{14}$ have the meaning given above of R$^{12}$ but do not represent hydrogen,
or, in the case where R$^{12}$, R$^{13}$ and R$^{14}$ do not represent hydrogen, E and/or T denote a group of the formula NR$^{34}$ in which R$^{34}$ with the exception of hydrogen has the meaning given above of R$^{12}$ and is identical to or different from it, or
R$^{34}$ denotes cyano or a group of the formula —CO$_2$R$^{35}$, in which
R$^{35}$ denotes benzyl or phenyl which are optionally substituted by nitro,
V and W have the meaning given above of D or denote the abovementioned group N—R$^{14}$ and are identical to or different from it,
a denotes a number 1 or 2,
b denotes a number 0 or 1,
R$^{15}$ and R$^{16}$ have the meaning given above of R$^{12}$ and are identical to or different from it,
and the tautomeric forms and salts thereof.
Very particularly preferred compounds of the general formula (I) are those in which
G, L and M represent hydrogen and the oxazolidinone radical is attached in position 5 or 6 to the phenyl ring.
Moreover, processes for the preparation of the compounds of the general formula (I) according to the invention have been found, characterized in that
[A] compounds of the general formulae (II) or (III)

or

in which
A has the meaning given above are reacted with lithium bromide/(C$_4$H$_9$)$_3$P(O) and epoxides of the general formula (IV)

in which
Q represents C$_1$–C$_6$-acyloxy in inert solvents, optionally in the presence of a base, and, in the case R$^1$=OH, the hydroxyl function is liberated by a typical ester hydrolysis or by a typical transesterification, or
[B] compounds of the general formula (V)

in which
A has the meaning given above and
X represents a typical protecting group, preferably benzyl, are reacted with epoxides of the general formula (IV), in inert solvents and in the presence of a base, for example lithium alkyls or lithium N-alkyl- or lithium N-silylalkylamides, preferably n-butyllithium, or
[C] in the case R$^1$=OH, compounds of the general formula (III) are first of all converted by elimination of nitrogen in alcohols into the compounds of the general formula (Va)

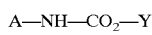 (Va)

in which

A has the meaning given above and

Y represents straight-chain or branched $C_1$–$C_6$-alkyl, preferably n-butyl, and in a second step as described under [A], are reacted in inert solvents and in the presence of a base, preferably lithium N-alkyl- or N-silylalkyl amides or n-butyllithium and epoxides of the general formula (IV), or

[D] compounds of the general formula (VI)

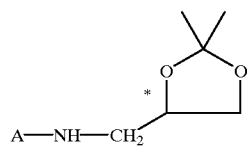 (VI)

in which

A has the meaning given above are either reacted directly with acids and diethyl carbonate, or first of all, by reacting the compounds of the general formula (VI) with acids, the compounds of the general formula (VII)

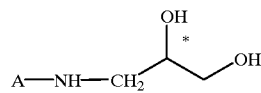 (VII)

in which

A has the meaning given above are prepared and are subsequently cyclized in the presence of an auxiliary in inert solvents, or

[E] compounds of the general formula (Ia)

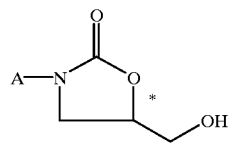 (Ia)

in which

A has the meaning given above are first of all converted, by reaction with ($C_1$–$C_4$)-alkyl- or phenylsulphonyl chlorides in inert solvents and in the presence of a base, into the corresponding compounds of the general formula (Ib)

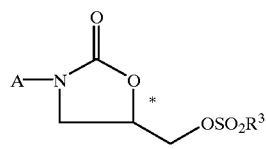 (Ib)

in which

A and $R^3$ have the meaning shown above, subsequently, using sodium azide in inert solvents, the azides of the general formula (Ic)

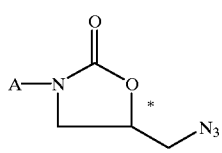 (Ic)

in which

A has the meaning given above are prepared, in a further step by reaction with ($C_1$–$C_4$-O)$_3$—P or PPh$_3$, preferably (CH$_3$O)$_3$P, in inert solvents and with acids, are converted into the amines of the general formula (Id)

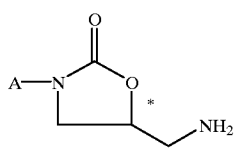 (Id)

in which

A has the meaning given above, and, by reaction with acetic anhydride or other acylating agents of the general formula (VIII)

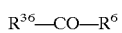 (VIII)

$R^{36}$—CO—$R^6$ in which $R^6$ has the meaning given above and $R^{36}$ represents halogen, preferably represents chlorine, or represents the radical —OCOR$^6$ in inert solvents the compounds of the general formula (Ie)

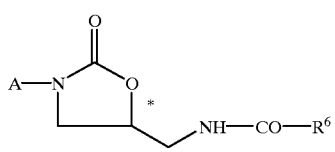 (Ie)

in which

A and $R^6$ have the meaning given above are prepared, or

[F] where A = 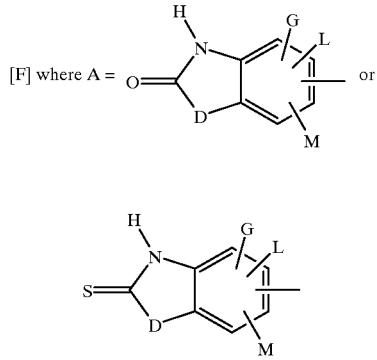

compounds of the general formula (IX)

(IX)
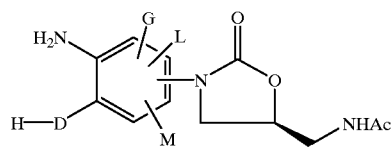

in which

G, L, M and D have the meaning given above are cyclized either using carbonyldiimidazole or thiocarbonyldiimidazole in dimethylformamide or by reaction with KS—$CO_2$—$C_2H_5$/$CH_3OH$ and subsequent addition of water, where A = 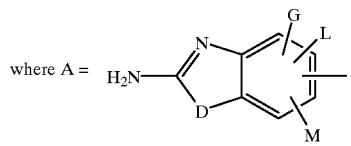

the compounds of the general formula (IX) are reacted with $BrCN/H_2O/CH_3OH$, or

[G] where $R^{12} \neq H$, starting from the compounds where $R^1$=NH—$COCH_3$, an acylation or alkylation with double bond displacement is carried out, or compounds of the general formula (I) having the radical

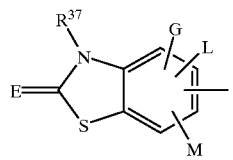

in which $R^{37}$ denotes $C_1$–$C_{10}$-alkyl, preferably $C_1$–$C_3$-alkyl, and E=O, compounds of the general formula (X)

(X)
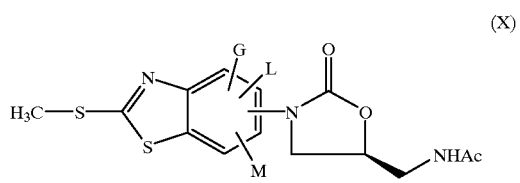

in which

G, L and M have the meaning given above, are first of all converted, by reaction with $C_1$–$C_{10}$-alkyl halides, preferably $C_1$–$C_3$-alkyl iodides, in inert solvents into the salts of the compounds of the general formula (XI)

(XI)
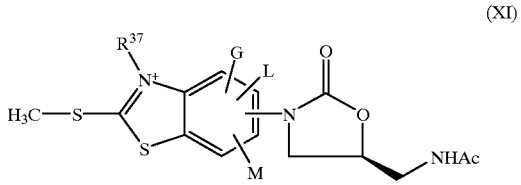

in which $R^{37}$ represents $C_1$–$C_{10}$-alkyl, preferably represents $C_1$–$C_3$-alkyl, and G, L and M have the meaning given above, and in a last step are reacted with methanol, and where E=S compounds of the general formula (XI) are subjected to thermolysis, and, in the case of the S-oxides, oxidation is carried out by a customary method, and, if desired, further substituents or functional groups which are already present are introduced and/or derivatized by customary methods, for example alkylation, redox reactions, substitution reactions and/or hydrolyses or introduction and elimination of protecting groups.

The processes according to the invention can be illustrated by way of example using the following equations:

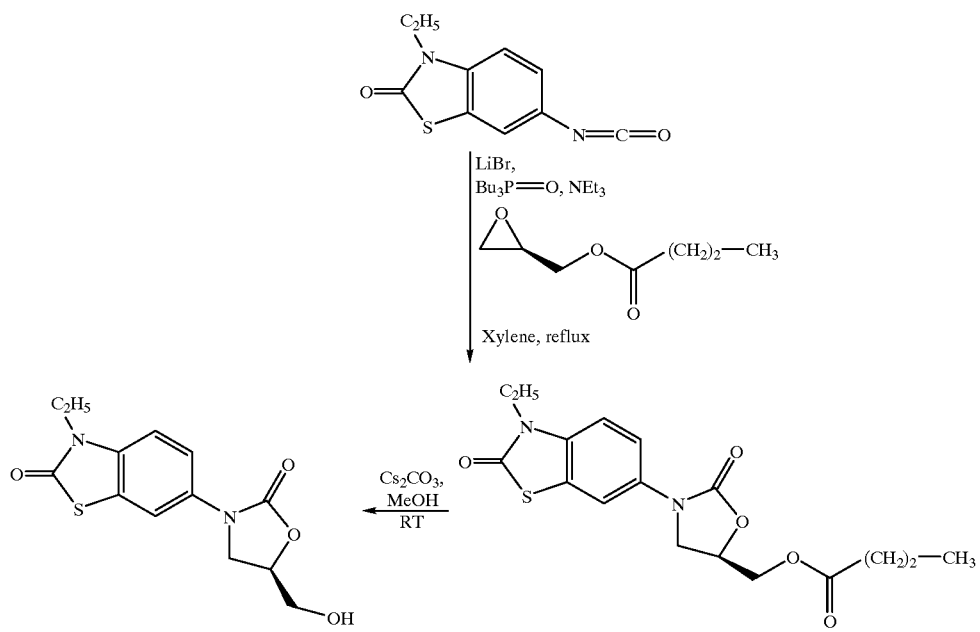
[A]
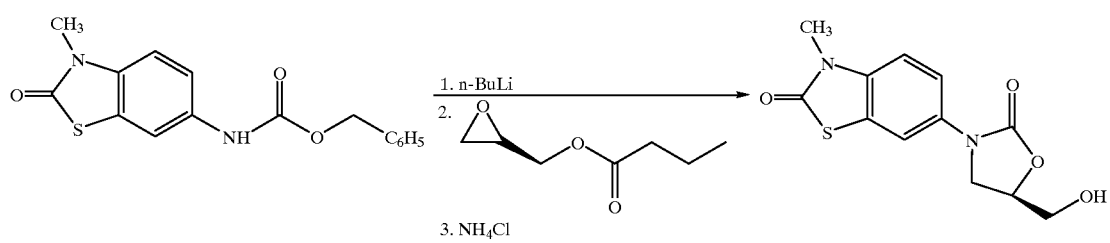
[B]
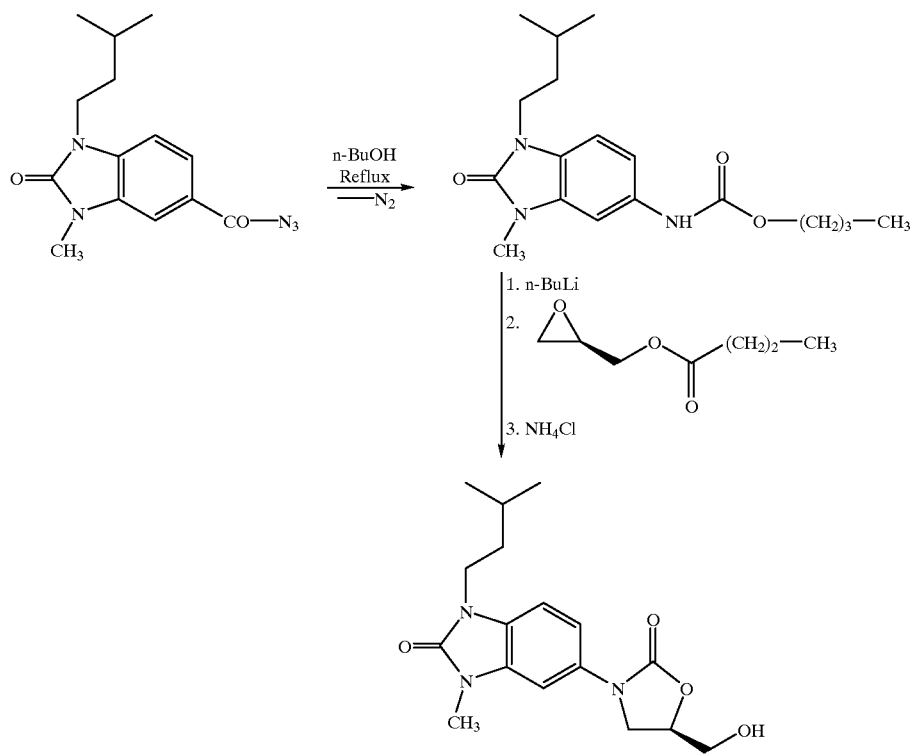
[C]

-continued
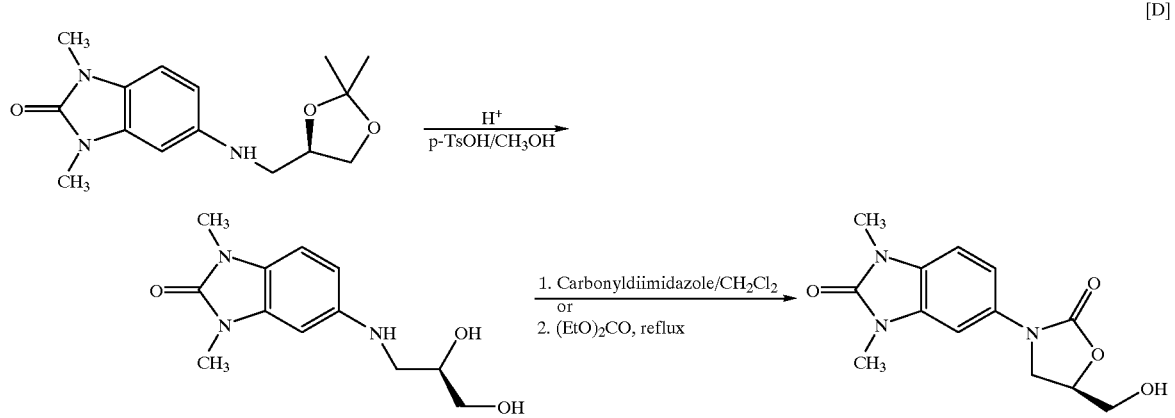
[D]
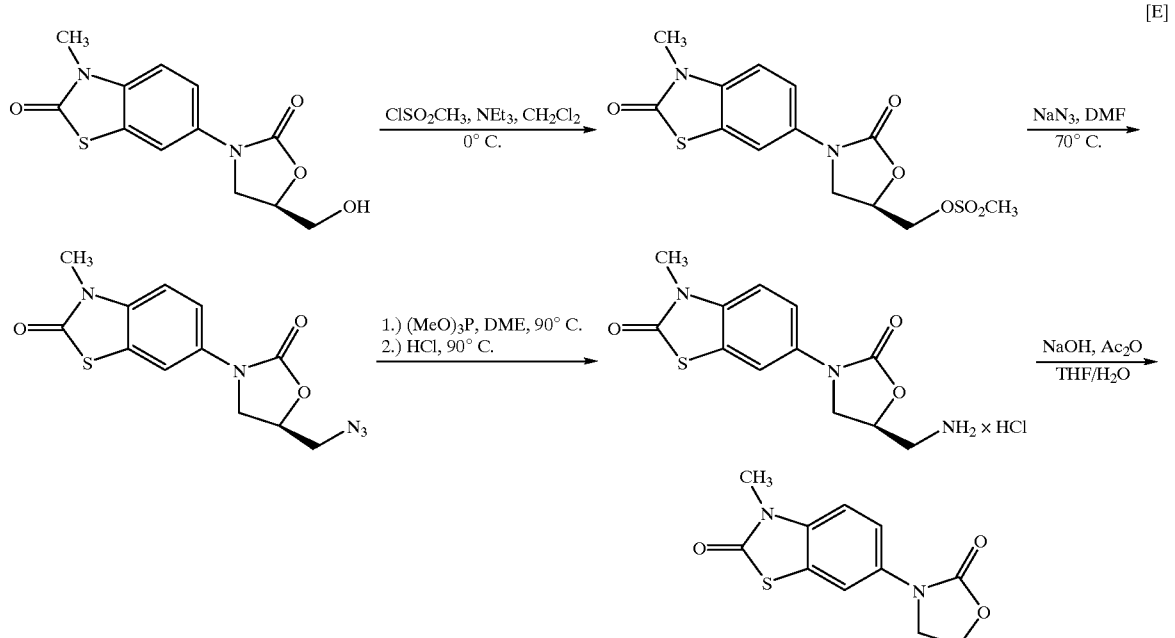
[E]
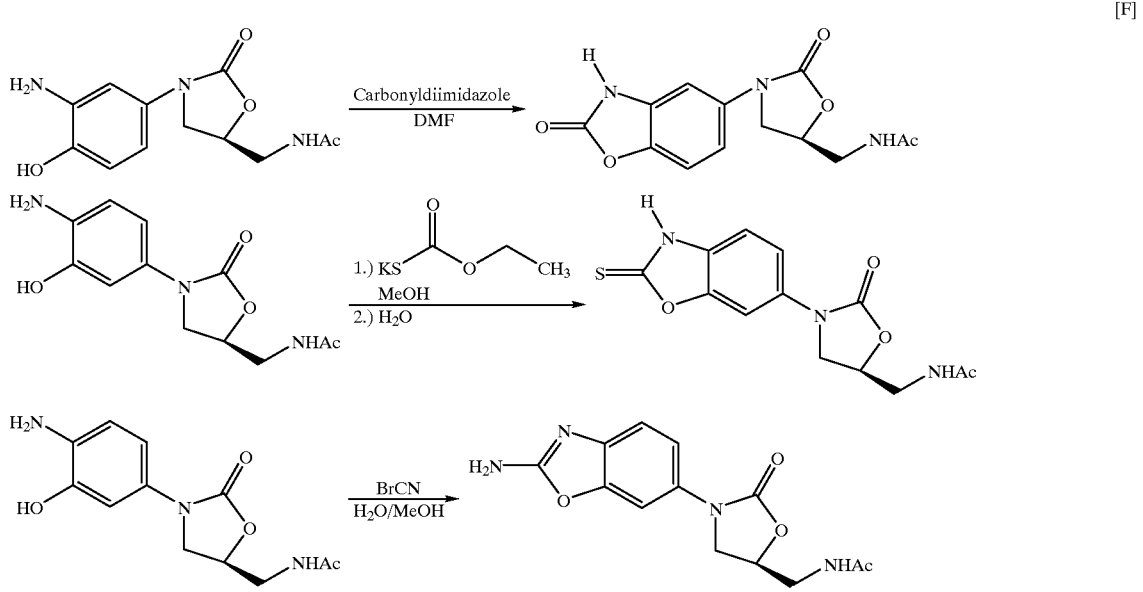
[F]

-continued

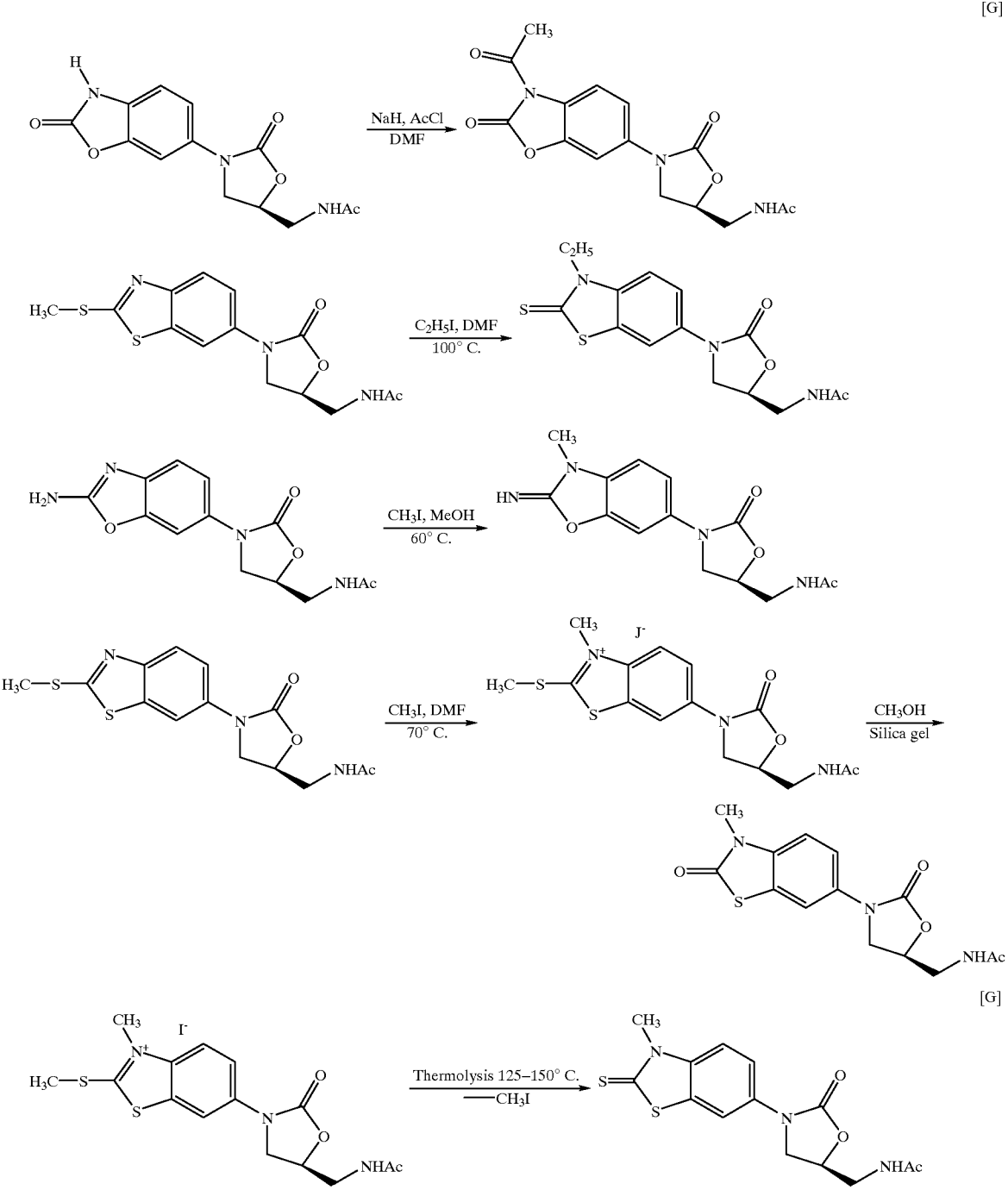

Suitable solvents depending on the individual process steps are the customary solvents, which do not change under the reaction conditions. They include, preferably, alcohols such as methanol, ethanol, propanol or isopropanol, or ethers such as diethyl ether, dioxane, 1,2-dimethoxyethane, tetrahydrofuran, glycol dimethyl ether or tert-butyl methyl ether, or ketones such as acetone or butanone, or amides such as dimethylformamide or hexamethyl-phosphoric triamide, or hydrocarbons such as hexane, benzene, dichlorobenzene, xylene or toluene, or dimethyl sulphoxide, acetonitrile, ethyl acetate, or halogenated hydrocarbons such as methylene chloride, chloroform or carbon tetrachloride, or pyridine, picoline or N-methylpiperidine. Mixtures of the solvents mentioned can also be used.

Suitable bases depending on the individual process steps are the customary inorganic or organic bases. They include, preferably, alkali metal hydroxide such as, for example, sodium hydroxide or potassium hydroxide, or alkali metal carbonates such as sodium carbonate, potassium carbonate, or alkali metal alcoholates such as, for example, sodium methanolate or potassium methanolate, or sodium ethanolate or potassium ethanolate, or organic amines such as ethyldiisopropylamine, triethylamine, picoline, pyridines or N-methylpiperidine, or amides such as sodium amide or lithium diisopropylamide, or lithium N-silylalkylamides such as, for example, lithium N-(bis)triphenylsilylamide, or lithium alkyls such as n-butyllithium.

The base is employed in a quantity of from 1 mol to 10 mol, preferably from 1 mol to 3 mol, based on 1 mol of the compounds of the general formulae (II), (III), (IV) and (Va).

All reactions are generally carried out at normal, elevated or at reduced pressure (e.g. 0.5 to 5 bar). Reactions are generally carried out at atmospheric pressure.

Process [A] is preferably carried out in xylene or dichlorobenzene, optionally in the presence of triethylamine, under reflux.

The base-catalyzed transesterification is carried out with one of the abovementioned alcohols, preferably methanol, in a temperature range from −10° C. to +40° C., preferably at room temperature.

Suitable bases in general are sodium hydrogen carbonate, sodium methanolate, hydrazine hydrate, potassium carbonate or caesium carbonate. Caesium carbonate is preferred.

Process [B] takes place in one of the abovementioned ethers using lithium alkyl compounds or lithium N-silylamides, such as, for example, n-butyllithium, lithium diisopropylamide or lithium bistrimethylsilylamide, preferably in tetrahydrofuran and lithium bis-trimethylsilylamide or n-butyllithium, in a temperature range from −100° C. to +20° C., preferably from −75° C. to −40° C.

For process [C], compounds suitable for the 1st step are preferably the abovementioned alcohols, and, in the case of the subsequent cyclization, tetrahydrofuran.

Suitable bases for the cyclization are preferably the abovementioned lithium N-silylalkyl compounds or n-butyllithium. Particular preference is given to n-butyllithium.

The first reaction step is carried out at the boiling point of the corresponding alcohol, and the cyclization is carried out in a temperature range from −70° C. to room temperature.

The cyclization [D] is carried out in the presence of an auxiliary and/or the presence of an acid.

Suitable acids are in general inorganic acids such as, for example, hydrochloric acid or sulphuric acid, or organic carboxylic acids having 1–6 carbon atoms, optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or aryl radicals, such as, for example, methanesulphonic acid, ethanesulphonic acid, benzenesulphonic acid or toluenesulphonic acid. Particular preference is given to hydrochloric acid.

The acid is employed in a quantity of from 1 mol to 10 mol, preferably from 1 mol to 2 mol, based on 1 mol of the compounds of the general formula (VI).

Suitable auxiliaries are the customary reagents such as phosgene, carbonyldiimidazole or diethyl carbonate or trichloromethyl chloroformate. Preference is given to carbonyldiimidazole, diethyl carbonate or trichloromethyl chloroformate.

Suitable solvents are the abovementioned halogenated hydrocarbons. Methylene chloride is preferred.

The cyclization reactions are generally carried out in a temperature range from −20° C. to 100° C., preferably at from −20° C. to room temperature.

The acylation [E] is in general carried out in one of the abovementioned ethers or halogenated hydrocarbons, preferably tetrahydrofuran or methylene chloride, in a temperature range from −30° C. to 50° C., preferably from −10° C. to room temperature.

The reductions are generally carried out using hydrides in inert solvents or using boranes, diboranes or their complex compounds.

The reductions can in general be carried out by hydrogen in water or in inert organic solvents such as alcohols, ethers or halogenated hydrocarbons, or mixtures thereof, using catalysts such as Raney nickel, palladium, palladium on animal charcoal or platinum, or using hydrides or boranes in inert solvents, optionally in the presence of a catalyst.

The reductions are preferably carried out using hydrides, such as complex borohydrides or aluminium hydrides and also boranes. Particular preference in this context is given to the use of sodium borohydride, lithium borohydride, sodium cyanoborohydride, lithium aluminium hydride, sodium bis-(2-methoxyethoxy)aluminium hydride or borane-tetrahydrofuran.

Reduction of the azides [E] is effected with $(CH_3O)_3P$ and hydrochloric acid.

The reduction takes place generally in a temperature range from −50° C. to a respective boiling point of the solvent, preferably from −20° C. to +90° C.

Suitable solvents in this context are all inert organic solvents which do not change under the reaction conditions. These include, preferably, alcohols such as methanol, ethanol, propanol or isopropanol, or ethers such as diethyl ether, dioxane, tetrahydrofuran, glycol dimethyl ether or diethylene glycol dimethyl ether, or amides such as hexamethylphosphoric triamide or dimethylformamide, or acetic acid. It is likewise possible to use mixtures of the solvents mentioned.

The hydroxy-protecting groups are generally eliminated by a customary method, for example by hydrogenolytic cleavage of the benzyl ether in the inert solvents listed above in the presence of a catalyst with hydrogen gas.

The amino-protecting group is generally eliminated likewise by customary methods, preferably, for instance, Boc with hydrochloric acid in dioxane, Fmoc with piperidine and Z with HBr/HOAc or by hydrogenolysis.

The other derivatization reactions listed above generally take place by the methods published in Compendium of Organic Synthetic Methods, T. T. Harrison and S. Harrison, Wiley Interscience.

Redox reactions, reductive amination, transesterification and the halogenation of methyl groups with N-bromosuccinimide (NBS) or N-chlorosuccinimide (NCS) are given as preferred and are explained by way of example below.

Suitable solvents for the alkylation are all customary organic solvents which do not change under the reaction conditions. These include, preferably, ethers such as diethyl ether, dioxane, tetrahydrofuran, glycol dimethyl ether, or hydrocarbons such as benzene, toluene, xylene, hexane, cyclohexane or petroleum fractions, or halogenated hydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, acetonitrile, acetone or nitromethane. Similarly, it is possible to use mixtures of the solvents mentioned. Preference is given to dichloromethane, dimethylsulphoxide and dimethylformamide.

The alkylation is carried out in the abovementioned solvents at temperatures from 0° C. to +150° C., preferably at room temperatures to +100° C., under atmospheric pressure.

The amidation and the sulfoamidation are in general carried out in inert solvents in the presence of a base and of a dehydrating agent.

Suitable solvents in this context are inert organic solvents which do not change under the reaction conditions. These include halogenated hydrocarbons such as dichloromethane, trichloromethane, tetrachloromethane, 1,1-dichloroethane, trichloroethane, tetrachloroethane, 1,2-dichloroethane or trichloroethylene, hydrocarbons such as benzene, xylene, toluene, hexane, cyclohexane, or petroleum fractions, nitromethane, dimethylformamide, acetonitrile or tetrahydrofuran. It is similarly possible to employ mixtures of the solvents. Particular preference is given to dichloromethane and tetrahydrofuran.

Suitable bases for the amidation and the sulfoamidation are the customary basic compounds. They include, preferably, alkali metal hydroxides and alkaline earth metal hydroxides such as lithium hydroxide, sodium hydroxide, potassium hydroxide or barium hydroxide, alkali metal hydrides such as sodium hydride, alkali metal carbonates or alkaline earth metal carbonates such as sodium carbonate, potassium carbonate, or alkali metal alcoholates such as, for example, sodium methanolate or sodium ethanolate, potassium methanolate or potassium ethanolate or potassium tert-butylate, or organic amines such as benzyltrimethylammonium hydroxide, tetrabutylammonium hydroxide, pyridine, triethylamine or N-methylpiperidine.

The amidation and the sulfoamidation are generally carried out in a temperature range from 0° C. to 150° C., preferably from 25° C. to 40° C.

The amidation and the sulfoamidation are in general carried out under atmospheric pressure. However, it is also possible to carry out the process under reduced pressure or under increased pressure (for example in a range from 0.5 to 5 bar).

When carrying out the amidation and the sulfoamidation, the base is generally employed in a quantity of from 1 to 3 mol, preferably from 1 to 1.5 mol, based on 1 mol of the respective carboxylic acid.

Suitable dehydrating reagents are carbodiimides such as, for example, diisopropyl carbodiimide, dicyclohexyl carbodiimide or N-(3-dimethylaminopropyl)-N'-ethylcarbodiimide hydrochloride, or carbonyl compounds such as carbonyldiimidazole, or 1,2-oxazolium compounds such as 2-ethyl-5-phenyl 1,2-oxazolium-3-sulphonate, or propanephosphoric anhydride or isobutyl chloroformate or benzotriazolyloxytris-(dimethylamino)phosphonium hexafluorophosphate, or phosphonic acid diphenylesteramide or methanesulphonyl chloride, optionally in the presence of bases such as triethylamine or N-ethylmorpholine or N-methylpiperidine or 4-dimethylaminopyridine.

Suitable bases for the hydrolysis are the customary inorganic bases. These include, preferably, alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate. Particular preference is given to employing sodium hydroxide or potassium hydroxide.

Suitable solvents for the hydrolysis are water or the organic solvents which are customary for a hydrolysis. These include, preferably, alcohols such as methanol, ethanol, propanol, isopropanol or butanol, or ethers such as tetrahydrofuran or dioxane, or dimethylformamide or dimethyl sulphoxide. It is particularly preferred to use alcohols such as methanol, ethanol, propanol or isopropanol. Similarly, it is possible to employ mixtures of the solvents mentioned.

The hydrolysis is in general carried out in a temperature range from 0° C. to +100° C., preferably from +20° C. to +80° C.

The hydrolysis is in general carried out at atmospheric pressure. However, it is also possible to work under reduced pressure or under increased pressure (e.g. from 0.5 to 5 bar).

When carrying out the hydrolysis, the base is generally employed in a quantity of from 1 to 3 mol, preferably from 1 to 1.5 mol, based on 1 mol of the ester. Particular preference is given to the use of molar quantities of the reactants.

Esterification is generally carried out using the corresponding alcohols in the presence of acids, preferably sulphuric acid, in a temperature range from 0° C. to 150° C., preferably from 50° C. to 100° C., under atmospheric pressure.

The compounds of the general formulae (IV) and (VIII) are known or can be prepared by customary methods.

The majority of the compounds of the general formula (VII) are novel, and they can be prepared, for example, as described above.

The compounds of the general formula (II) are in some cases known and in some cases novel and in this case can be prepared, for example, by reacting the corresponding amines with trichloroethyl chloroformate in one of the abovementioned solvents, preferably xylene, at reflux temperature.

The compounds of the general formula (III) are in some cases known or are novel and can then be prepared, for example, starting from the corresponding carboxylic acids, by reaction either with isobutyl chloroformate/acetone, sodium azide/water or with diphenylphosphoryl azide/tetrahydrofuran or with xylene or methylene chloride in the presence of one of the abovementioned bases, preferably triethylamine, at from –10° C. to room temperature.

The compounds of the general formulae (V) and (Va) are in some cases known or are novel and can be prepared either by elimination of nitrogen from the corresponding carboxylic acid azides and reaction with the corresponding alcohols, or by reacting the corresponding amines with chloroformic esters, preferably benzyl chloroformate, in one of the abovementioned solvents, preferably tetrahydrofuran or dioxane, in a temperature range from –10° C. to 200° C., preferably from 0° C. to 150° C.

The compounds of the general formula (Ia) are novel and can be prepared, for example, as described under [A], [B], [D] or [E].

The compounds of the general formula (Ib), (Ic), (Id) and (Ie) are novel and can be prepared as described above.

The compounds of the general formula (VI) are to a large extent known or are novel and can be prepared, for example, starting from the free amines (Ia) either by reaction with the acetonide of glyceraldehyde in methanol and in the presence of sodium acetate/sodium cyanoborohydride or of sodium boranate and methanol in a temperature range from –20° C. to +40° C., preferably from –10° C. to 20° C., under atmospheric pressure.

The reaction of the compounds of the general formula (IX) [F] takes place in a temperature range from –10° C. to 150° C., preferably from 10° C. to 60° C., under atmospheric pressure.

The compounds of the general formula (IX), although included by the scope of definition of EP 609 905, are novel as concrete compounds and can be prepared in analogy to the abovementioned process [E] by using acetyl chloride.

The acylations [G] take place in general in one of the solvents listed above, preferably dimethylformamide, in the presence of a base, preferably sodium hydride, in a temperature range from 0° C. to 150° C., preferably from 20° C. to 80° C., under atmospheric pressure.

The alkylations with double bond displacement take place, depending on the radical A, in one of the abovementioned solvents, preferably dimethylformamide or methanol, in a temperature range from 30° C. to 150° C., preferably from 50° C. to 110° C., under atmospheric pressure.

The reaction to give the compounds of the general formula (XI) [G] takes place in one of the abovementioned solvents, preferably dimethylformamide, in a temperature range from −10° C. to 150° C., preferably from 20° C. to 70° C., under atmospheric pressure.

The thermolysis [G] takes place in a temperature range from 80° C. to 200° C., preferably from 125° C. to 150° C.

Oxidation to the S-oxide takes place in general in one of the abovementioned solvents, preferably in methylene chloride, using oxidizing agents such as, for example, metachloroperbenzoic acid, hydrogen peroxide, peracetic acid or Oxone, preferably with metachloroperbenzoic acid, in a temperature range from 0° C. to 80° C., preferably from 20° C. to 60° C.

The compounds of the formula (X) are novel as concrete compounds and can be prepared in analogy to process [E] listed above.

The compounds of the general formula (XI) are novel and can be prepared as described above.

The minimum inhibitory concentration (MIC) were determined by a series dilution method on Iso-Sensitest agar (Oxoid). For each test substance, a series of agar plates each comprising concentrations of the active compound decreasing by double dilution in each case was prepared. The agar plates were inoculated with a multipoint inoculator (Denley). Overnight cultures of the pathogens which had been diluted beforehand such that each inoculation point comprised about $10^4$ colony-forming particles were used for the inoculation. The inoculated agar plates were incubated at 37° C. and the germ growth was read off after about 20 hours. The MIC value (µg/ml) indicates the lowest active compound concentration at which no growth was detectable with the naked eye.

The microtiter plates were incubated at 37° C. and read off after about 20 hours (Staph) or after 3 to 5 days (Mycobacterium). The MIC value (µg/ml) indicates the lowest concentration of active substance at which no growth was detectable.

| | | | MIC values (µg/ml): | | | | |
|---|---|---|---|---|---|---|---|
| Ex. No. | Staph. 133 | Staph. 48N | Staph. 25701 | Staph. 9TV | E. coli Neumann | Klebs. 57 USA | Psdm. Bonn |
| 17 | 8 | 8 | 8 | 8 | >64 | >64 | >64 |
| 18 | 0.25 | 0.25 | 0.25 | 0.06 | >64 | >64 | >64 |
| 22 | 1 | 1 | 1 | 0.5 | >64 | >64 | >64 |
| 24 | 8 | 16 | 16 | 16 | >64 | >64 | >64 |
| 37 | 1 | 1 | 1 | 0.5 | 16 | 64 | 64 |
| 38 | 4 | 4 | 4 | 1 | >64 | >64 | >64 |
| 39 | 4 | 4 | 4 | 4 | >64 | >64 | >64 |
| 43 | 0.25 | 0.125 | 0.25 | 0.125 | >32 | >64 | >64 |
| 44 | 0.5 | 0.5 | 0.5 | 0.5 | >64 | >64 | >64 |
| 38 | 4 | 4 | 4 | 1 | >64 | >64 | >64 |
| 47 | 0.5 | 0.5 | 0.5 | 0.25 | 32 | 64 | >64 |
| 56 | 0.5 | 0.5 | 0.5 | 0.25 | 64 | >64 | >64 |
| 70 | 0.5 | 0.5 | 0.5 | 0.5 | >64 | >64 | >64 |
| 62 | 1 | 1 | 1 | 0.5 | >64 | >64 | >64 |
| 84 | 1 | 1 | 1 | 0.5 | 64 | >64 | >64 |
| 94 | 0.5 | 0.5 | 0.5 | 0.25 | 64 | >64 | >64 |

| | MIC values (µg/ml) | | | | | |
|---|---|---|---|---|---|---|
| | Organism: Mycobacterium smegmacis | | | | | |
| Ex. No. | DSM 43061 | DSM 43078 | DSM 43277 | DSM 43299 | DSM 43464 | DSM 43465 |
| 18 | 0.25 | 0.25 | 0.25 | 1 | 1 | 0.5 |
| 56 | 1 | 1 | 0.25 | 1 | 4 | 0.5 |
| 54 | 4 | 1 | 2 | 4 | 16 | 4 |
| 70 | 0.25 | 0.125 | 0.5 | 2 | 8 | 1 |

The compounds according to the invention of the general formulae (I), (Ia), (Ib), (Ic), (Id) and (Ie) couple low toxicity with a broad antibacterial spectrum, especially against Gram-positive bacteria and Mycobacteria, corynebacteria, Haemophilus influenzae and anaerobic organisms. These properties enable them to be used as chemotherapeutic active substances in human and veterinary medicine.

The compounds according to the invention are active against a broad spectrum of microorganisms. They can be used to control Gram-positive bacteria and bacteria-like microorganisms, such as mycoplasms, and to prevent, alleviate and/or cure the diseases caused by the pathogens.

The compounds according to the invention are particularly effective against bacteria and bacteria-like microorganisms. They are therefore particularly suitable in human and veterinary medicine for the prophylaxis in chemotherapy of local and systemic infections caused by such pathogens.

The present invention includes pharmaceutical formulations which, in addition to nontoxic, inert pharmaceutically appropriate excipients, comprise one or more compounds according to the invention or which consist of one or more active substances according to the invention, and also processes for the preparation of these formulations.

If appropriate, the active substance or substances can also be in microencapsulated form in one or more of the abovementioned excipients.

The therapeutically active compounds should preferably be present in the abovementioned pharmaceutical formulations in a concentration of about 0.1 to 99.5% by weight, preferably about 0.5 to 95% by weight, of the overall mixture.

In addition to the compounds according to the invention, the pharmaceutical formulations indicated above can also comprise further pharmaceutical active substances.

In general, it has proved advantageous in both human and veterinary medicine to administer the active substance or substances according to the invention in overall quantities of from about 0.5 to about 500 mg, preferably from 5 to 100 mg, per kg of body weight every 24 hours, if appropriate in the form of a plurality of individual doses, in order to achieve the desired results. An individual dose comprises the active substance or substances according to the invention preferably in quantities of from about 1 to about 80 mg, in particular from 3 to 30 mg, per kg of body weight.

The compounds according to the invention can also be combined with other antibiotics for the purpose of expanding the spectrum of action and in order to achieve an increase in action.

APPENDIX TO THE EXPERIMENTAL SECTION

List of the eluent mixtures used for chromatography:

I dichloromethane:methanol
II toluene:ethyl acetate
III acetonitrile:water
IV ethyl acetate
V petroleum ether:ethyl acetate
VI dichloromethane:ethanol
VII toluene:ethanol
VIII toluene:ethanol:triethylamine
Abbreviations:
Z benzyloxycarbonyl
Boc tert-butoxycarbonyl
DMF dimethylformamide
Ph phenyl
Me methyl
THF tetrahydrofuran
CDI carbonyldiimidazole
DCE dichloroethane

STARTING COMPOUNDS
Example I 6-(Benzyloxycarbonylamino)-3-methyl-2-benzothiazolinone

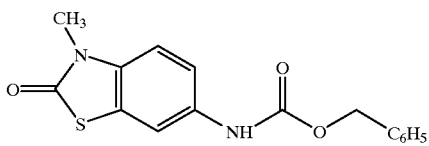

1.3 ml (9.10 mmol) of benzyl chloroformate are added dropwise at 0° C. to 1.76 g (8.12 mmol) of 6-amino-3-methyl-2(3H)-benzothiazolone hydrochloride (J. Heterocyclic Chem. 1992, 29, 1069) in 17 ml of water, 14 ml of THF and 17 ml of saturated $NaHCO_3$ solution. After 1 h, 120 ml of water are added, the THF is stripped off in vacuo, and the precipitate is filtered off with suction, washed three times with water and twice with petroleum ether and dried at 60° C.

Yield: 2.44 g (96%)
M.p.: 183° C.
$R_f$ (II, 7:3)=0.39
$^1$H-NMR ([$D_6$] DMSO): $\delta$=7.77 (d, J=1 Hz, 1H, benzothiazolinone 7-H); 7.23–7.45 (m, 6H, Ph), 7.22 (d, J=6 Hz, 1H, benzothiazolinone 4-H); 5.15 (s, 2H); 3.38 (s, 3H—$CH_3$).

The compounds listed in Table I are obtained as described for Example I from the corresponding amines with benzyl chloroformate:

TABLE I

| Ex. No. | A | Yield (% of th.) | m.p. (° C.) | $R_f$ (eluent, ratio) | MS (DCI, $NH_3$) m/z (M + H)$^+$ |
|---|---|---|---|---|---|
| II | (1,3-dimethyl-2-oxo-benzimidazol-5-yl, N-CH₃, NH) | 96 | 241 | 0.24 (I, 95:5) | 298 |
| III | (1-ethyl-3H-2-oxo-benzimidazol-5-yl, N-C₂H₅, NH) | 99 | 211 | 0.43 (I, 9:1) | 312 |
| IV | (2-methylthio-benzothiazol-6-yl, H₃C—S) | 96 | 111 | 0.71 (II, 1:4) | 331 |

Example V 5-(Benzyloxycarbonylamino)-1,3-dimethyl-2-benzimidazolinone

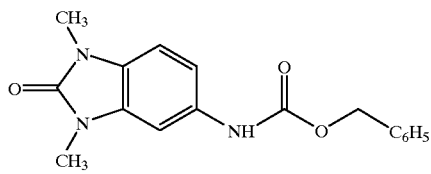

A stirred suspension of 2.49 g (8.37 mmol) of the compound from Example II, 3.47 g (25.11 mmol) of potassium carbonate and 1.90 ml (30.97 mmol) of iodomethane in 50 ml of ethanol is heated at reflux for 1.5 h. The mixture may cool down, and the solids are separated off by filtration at a temperature of 30° C. and the filtrate is concentrated in vacuo. The residue is dissolved in 50 ml of dichloromethane, the solution is stirred thoroughly with MgSO$_4$, and after solvent is removed by evaporation the residue is dried over Sicapent in a high vacuum. 2.28 g (87%) of the title compound are obtained as colourless crystals.

m.p.: 176° C.

$R_f$=0.48 (dichloromethane:methanol 95:5)

MS (EI, 70 eV) m/z=311 (M)$^+$ $^1$H-NMR (200 MHz, [D$_6$] DMSO): δ=9.70 (bs, 1H, NHCO); 7.40 (m, 6H, H arom.); 7.01 (s, 2H, H arom.); 5.12 (s, 2H, CH$_2$); 3.30, 3.31 (2s, 6H, NCH$_3$).

The compounds listed in Table II are obtained as described for Example V by alkylation of the compounds from Table I:

Example VIII

5-Butyloxycarbonylamino-1-(3'-methylbutyl)-2-benzimidazolinone

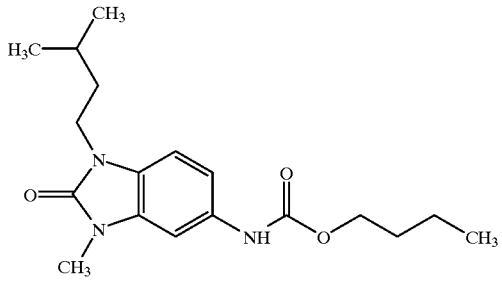

1.1 ml (7.8 mmol) of isobutyl chloroformate in 5 ml of acetone are added dropwise slowly to a solution, cooled to 0° C., of 1.58 g (6.0 mmol) of the compound from Example VI and 1.0 ml (7.21 mmol) of triethylamine in 12 ml of acetone. The mixture is stirred at 0° C. for 45 min and then 586 mg (9.02 mmol) of sodium azide in 3 ml of water are added dropwise slowly. This mixture is stirred at 0° C. for 1 hour and added to 50 ml of ice-water. The mixture is extracted with xylene (3×2 ml) and the combined organic phases are dried over MgSO$_4$. This solution is then added dropwise slowly to 20 ml of boiling n-butanol (vigorous evolution of gas). When the addition is complete the mixture is boiled under reflux for 10 min and cooled to RT and the n-butanol is stripped off on a rotary evaporator. The residue is chromatographed on 85 g of silica gel. 448 mg (22%) of a colourless oil are obtained.

$R_f$ (II, 7:3)=0.25

TABLE II

| Ex. No. | Compound | Yield (% of th.) | m.p. (° C.) | $R_f$ (eluent, ratio) | MS (CI) m/z (M + H)$^+$ |
|---|---|---|---|---|---|
| VI | [structure: 1-(3'-methylbutyl)-3-methyl-2-benzimidazolinone-5-COOH] | 77 | / | 0.31 (I, 9:1) | 265 |
| VII | [structure: 1-ethyl-3-benzyl-2-benzimidazolinone-5-NH—CO$_2$—CH$_2$—C$_6$H$_5$] | 75 | 147 | 0.44 (I, 97:3) | 402 |

MS (CI): m/z=334 (M$^+$+H)

$^1$H-NMR ([D$_6$] DMSO): δ=9.50 (bs, 1H, NH); 7.32 (bs, 1H, Ph); 7.00 (bs, 2H, Ph); 4.10 (t, J=7 Hz, 2H, CH$_2$); 3.80 (t, J =6 Hz, 2H, CH$_2$); 3.32 (s, 3H, NCH$_3$); 1.30–1.72 (m, 8H); 0.80–1.10 (m, 11H).

The compounds listed in Table III are obtained as described for Example VIII by reaction of the corresponding acids:

TABLE III

| Ex. No. | Compound | Yield (% of th.) | m.p. (° C.) | $R_f$ (eluent, ratio) | MS (DCI, $NH_3$) m/z $(M + H)^+$ |
|---|---|---|---|---|---|
| IX | $O_2N$–Ph(–O–$CH_2$–$C_6H_5$)–NH–C(=O)–O–$(CH_2)_3$–$CH_3$ | 78 | 121–122 | 0.67 (VII, 95:5) | 345 |
| X | $O_2N$–Ph(–O–$CH_2$–$C_6H_5$)–NH–C(=O)–O–$(CH_2)_3$–$CH_3$ | 63 | 133 | 0.51 (VII, 95:5) | 345 |

Example XI (5R)-3-(4-Benzyloxy-3-nitrophenyl)-5-(hydroxymethyl)-oxazolidin-2-one

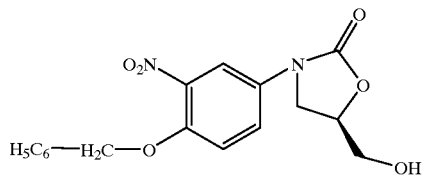

23.0 g (66.7 mmol) of the compound from Example IX are dissolved in 200 ml of THF and the solution is cooled to 0° C. About 68 ml of 1.0 M LiHMDS solution in THF are then added dropwise slowly. 9.5 ml (68 mmol) of (R)-glycidyl butyrate are then added dropwise. The mixture is allowed to rise to RT, saturated ammonium chloride solution is added, and the THF is stripped off in vacuo. The resulting precipitate is filtered off with suction, washed with water and ether and dried in a high vacuum.

Yield: 20.85 g (91%)

m.p.: 128–130° C.

$R_f$ (II, 1:1)=0.21

MS (FAB): m/z=345 (M+)

$^1$H-NMR ([$D_6$] DMSO): δ=8.0 (d, 1H, Ph), 7.62 (d, 1H, Ph), 7.30–7.50 (m, 6H, Ph), 5.30 (s, 2H, $CH_2$); 5.25 (t, 1H, OH); 4.68–4.80 (m, 1H, 5-H); 4.15 (t, 1H, 4-H); 3.90 (dd, 1H, 4-H); 3.55–3.75 (m, 2H, $CH_2O$).

The compounds listed in Table IV are prepared in analogy to the instructions of Example XI:

TABLE IV

| Ex. No. | A | Yield (% of th.) | m.p. (° C.) | $R_f$ (eluent, ratio) | $[\alpha]^{20}_D$ (DMSO) | MS (FAB) m/z $(M^+ + H)$ |
|---|---|---|---|---|---|---|
| XII | $O_2N$–Ph(–O–$CH_2$–$C_6H_5$)–$CH_3$ | 73 | 137–139 | 0.28 (II, 1:1) | −38.1 (c = 0.985) | 345 |

TABLE IV-continued

[Structure: oxazolidin-2-one with A-N substituent and -OH on 5-position methyl]

| Ex. No. | A | Yield (% of th.) | m.p. (°C.) | $R_f$ (eluent, ratio) | $[\alpha]^{20}_D$ (DMSO) | MS (FAB) m/z (M⁺ + H) |
|---|---|---|---|---|---|---|
| XIII | H₃C—S—[6-methylbenzothiazol-2-yl] | 67 | 156 | 0.24 (II, 1:4) | | 297 |

Example XIV (5R)-3-(4-Benzoyloxy-3-nitrophenyl)-5-(methylsulphonyloxymethyl)oxazolidin-2-one

[Structure: O₂N-substituted phenyl with H₅C₆—H₂C—O— group, attached to oxazolidin-2-one with —O—SO₂—CH₃]

23.6 ml (230 mmol) of methanesulphonyl chloride are added slowly to a solution, cooled to 0° C., of 71.5 g (208 mmol) of the compound from Example XI and 35 ml (250 mmol) of triethylamine in 650 ml of anhydrous THF. The mixture is stirred at 0° C. for 3 h and added to ice-water. The resulting precipitate is filtered off with suction, washed with water and toluene and dried in a high vacuum.

Yield: 65.8 g (75%)

m.p.: 149–150° C.

$R_f$ (VII, 5:1)=0.36

MS (FAB): m/z=423 (M⁺)

¹H-NMR ([D₆] DMSO): δ=8.12 (d, J=1 Hz, 1H, Ph); 7.75 (dd, J=6 Hz, J=1 Hz, 1H, Ph); 7.35–7.55 (m, 6H, Ph); 5.30 (s, 2H, CH₂); 4.40–4.60 (m, 2H, CH₂O); 4.22 (t, J=9 Hz, 1H, 4-H); 3.85 (dd, J=9 Hz, J=5 Hz, 1H, 4-H); 3.25 (s, 3H, SO₂CH₃).

The compounds listed in Table V are prepared in analogy to the instructions of Example XIV:

TABLE V

[Structure: oxazolidin-2-one with A-N substituent and —O—SO₂—CH₃ on 5-position methyl]

| Ex. No. | A | Yield (% of th.) | m.p. (°C.) | $R_f$ (eluent, ratio) | $[\alpha]^{20}_D$ (DMSO) | MS (FAB) m/z (M⁺ + H) |
|---|---|---|---|---|---|---|
| XV | O₂N-phenyl with C₆H₅—CH₂—O— and methyl substituents | 92 | 140–142 | 0.34 (VII, 5:1) | −48.8 (c = 1.01) | 423 |
| XVI | H₃C—S—[6-methylbenzothiazol-2-yl] | 82 | 106 | 0.41 (I, 95.5) | / | 375 |

Example XVII (5R)-3-(4-Benzyloxy-3-nitrophenyl)-5-(azidomethyl)oxazolidin-2-one

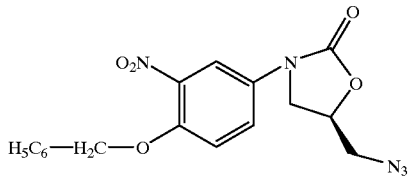

4.4 g (66.9 mmol) of sodium azide are added to a solution of 25.7 g (60.8 mmol) of the compound from Example XI in 200 ml of anhydrous DMF, and the mixture is stirred at 70° C. for 12 h. It is cooled to room temperature and 200 ml of ice-water are stirred in. The resulting precipitate is filtered off, washed with water and petroleum ether and dried in vacuo.

Yield: 21.4 g (95%)

m.p.: 158–160° C.

$R_f$ (VII, 5:1)=0.48

MS (EI): m/z=370 (M$^+$)

$^1$H-NMR ([D$_6$] DMSO): δ=8.05 (d, 1H, J=8 Hz, Ph); 7.25–7.50 (m, 7H, Ph); 5.30 (s, 2H, CH$_2$); 4.85–5.05 (m, 1H, 5-H); 4.23 (t, J=9 Hz, 1H, 4-H); 3.55–3.90 (m, 3H, 4-H, CH$_2$N$_3$).

The compounds listed in Table VII are prepared in analogy to the instructions of Example XVII:

A solution of 53.1 g (144 mmol) of the compound from Example XVII in 160 ml of 1,2-dimethoxyethane is heated to 50° C. 20.4 ml (173 mmol) of trimethyl phosphite are added dropwise slowly (gas evolution) and, after addition is complete, the mixture is stirred at 90° C. for 2 h. 36 ml of 6 N HCl are then added dropwise, and stirring is continued at 90° C. for 22 h. The mixture is cooled to room temperature, 810 ml of 0.1 N HCl are added, and the aqueous phase is washed with ether (3×320 ml) and subsequently adjusted to pH=9. The aqueous phase is extracted (2×300 ml) with ethyl acetate (3×650 ml), and the combined organic phases are washed with saturated NaCl solution (1×100 ml) and dried (Na$_2$SO$_4$). The solvents are stripped off in vacuo and the residue is dried in a high vacuum.

Yield: 47.2 g (96%)

m.p.: 135–136° C.

$R_f$ (VIII, 85:10:5)=0.05

MS (EI): m/z=344 (M$^+$)

$^1$H-NMR ([D$_6$] DMSO): δ=8.3–9.1 (bs, 3H, NH$_3$); 8.15 (d, 1H, Ph); 7.3–7.8 (m, 7H, Ph); 5.30 (v, 2H, CH$_2$); 4.9–5.1 (m, 1H, 4-H); 4.20 (m, 1H, 5-H); 4.00 (m, 1H, 5-H); 3.10–3.40 (m, 2H, CH$_2$N).

The compounds listed in Table VIII are prepared in analogy to the instructions of Example XX:

TABLE VII

| Ex. No. | A | Yield (% of th.) | m.p. (° C.) | $R_f$ (eluent, ratio) | $[α]^{20}_D$ (DMSO) | MS (FAB) m/z (M$^+$ + H) |
|---|---|---|---|---|---|---|
| XVIII | O$_2$N–, H$_5$C$_6$–H$_2$C–O– (phenyl) | 92 | 138–140 | 0.26 (VII, 5:1) | −119.4° (c = 1.1) | 370 |
| XIX | H$_3$C–S– (benzothiazole, methyl) | 95 | 136 | 0.59 (I, 95:5) | / | 322 |

Example XX (5S)-3-(4-Benzyloxy-3-nitrophenyl)-5-(aminomethyl)oxazolidin-2-one

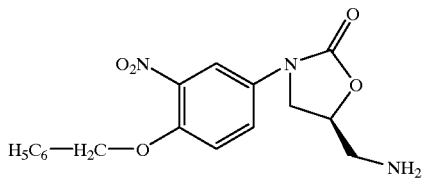

TABLE VIII

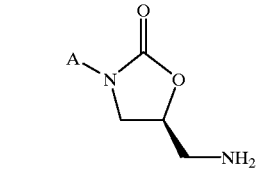

| Ex. No. | D | Yield (% of th.) | m.p. (° C.) | R$_f$ (eluent, ratio) | MS (FAB) m/z (M$^+$) |
|---|---|---|---|---|---|
| XXI | 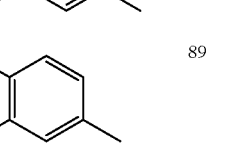 | 83 | 110 | 0.09 (III, 9:1) | |
| XXII | 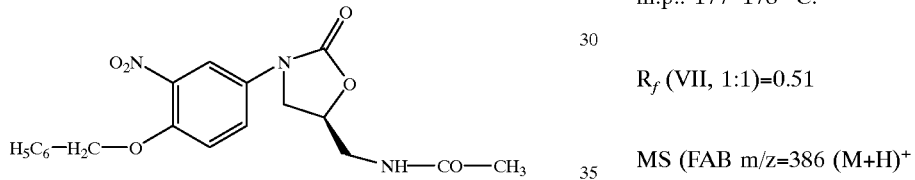 | 89 | 132–134 | 0.08 (VIII, 85:10:5) | 344 |

Example XXIII (5S)-3-(4-Benzyloxy-3-nitrophenyl)-5-(acetylaminomethyl)oxazolidin-2-one

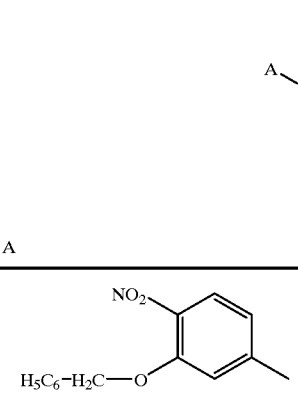

14.6 ml (205 mmol) of acetyl chloride are added dropwise slowly to a solution, cooled to 0° C., of 47.2 g (137 mmol) of the compound from Example XX and 29.04 ml (212 mmol) of triethylamine in 500 ml of anhydrous THF. The mixture is stirred at 0° C. for 2 h and added to ice-water. The precipitate is filtered off with suction, washed with water and ether and dried over P$_2$O$_5$ in a high vacuum.

Yield: 48.9 g (93%)

m.p.: 177–178° C.

R$_f$ (VII, 1:1)=0.51

MS (FAB m/z=386 (M+H)$^+$ $^1$H-NMR ([D$_6$] DMSO): δ=8.24 (t, J=4 Hz, 1H, NH); 8.10 (d, J=1 Hz, 1H, Ph); 7.75 (dd, J=6 Hz, 1H, Ph); 7.20–7.50 (m, 6H, Ph); 5.30 (s, 2H, CH$_2$); 4.70–4.80 (m, 1H, 5-H); 4.15 (t, J=9 Hz, 1H, 4-H); 3.70 (dd, J=9 Hz, J=5 Hz, 1H, H-4); 3.35–3.50 (m, 5H, CH$_2$N, NCH$_3$); 1.83 (s, 3H, COCH$_3$).

The compounds listed in Table IX are prepared in analogy to the instructions of Example XXIII:

TABLE IX

| Ex. No. | A | Yield (% of th.) | m.p. (° C.) | R$_f$ (eluent, ratio) | [α]$^{20}$$_D$ (DMSO) | MS (FAB) m/z (M$^+$ + H) |
|---|---|---|---|---|---|---|
| XXIV | NO$_2$, H$_5$C$_6$–H$_2$C–O— | 86 | 155–156 | 0.62 (VII, 1:1) | −23.6° (c = 1.05) | 386 |

TABLE IX-continued

[Structure: A-N-oxazolidinone-CH2-NH-C(O)-CH3]

| Ex. No. | A | Yield (% of th.) | m.p. (° C.) | $R_f$ (eluent, ratio) | $[\alpha]^{20}_D$ (DMSO) | MS (FAB) m/z (M$^+$ + H) |
|---|---|---|---|---|---|---|
| XXV | H3C—S—[benzothiazole-methyl] | 83 | 136 | 0.15 (I, 95:5) | | 338 |

Example XXVI (5S)-3-(2-Methythio-3methyl-benzothiazol-6-yl)-5-(acetylaminomethyl)oxazolidin-2-one iodide

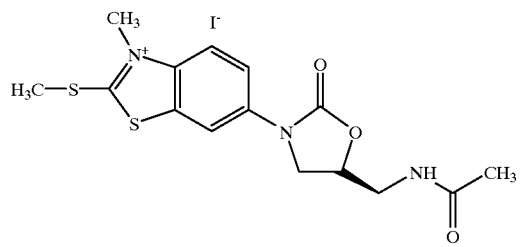

2.6 ml (40.00 mmol) of iodomethane are added to a stirred solution of 1.35 g (4.00 mmol) of the compound from Example XXV in 6 ml of anhydrous DMF and the mixture is heated at 70° C. for 23 h. The reaction mixture must subsequently cool down, 80 ml of ether are added, and the resulting precipitate is separated off by filtration. It is stirred into 50 ml of ethanol, filtration is carried out again, the product is dried in a high vacuum over Sicapent to give 1.17 g (61%) of the title compound as colourless crystals.

m.p.: 149° C. (decomposition)

MS (FAB) m/z=352 (cation M$^+$)

$^1$H-NMR (250 Mz, [D$_6$] DMSO): δ=8.60 (d, J=1 Hz, 1H, benzothiazole H-7); 8.28 (m, 1H, NHCO); 8.20 (d, J=10 Hz, 1H, benzothiazole H-4); 8.02 (dd, J=1 Hz, J=10 Hz, 1H, benzothiazole H-5); 4.82 (m, 1H, H-5); 4.20 (t, J=10 Hz, 1H, H-4 cis); 4.10 (s, 3H, NCH$_3$); 3.85 (dd, J=7 Hz, J=10 Hz, 1H, H-4 trans); 3.46 (m, 2H, CH$_2$N); 3.12 (s, 3H, SCH$_3$); 1.85 (s, 3H, COCH$_3$).

Example XXVII (5S)-3-(3-Amino-4-hydroxphenyl)-5-(acetylaminomethyl)-oxazolidin)2-one

[Structure: H2N, HO-phenyl-N-oxazolidinone-CH2-NH-C(O)-CH3]

3.58 g (9.28 mmol) of the compound from Example XXIII and 350 mg of Pd—C (10%) are stirred in 100 ml of methanol and 100 ml of THF under hydrogen (1 atm) for 3 h. The catalyst is removed by filtration, the solvent is stripped off and the residue is dried.

Yield: 2.5 g (quant.)

$R_f$ (VII, 1:1)=0.42

MS (CI): m/z=265 (M$^+$)

$[\alpha]_D^{20}$=−110.45 (c=1.0, DMSO)

$^1$H-NMR ([D$_6$] DMSO): δ=9.0–9.5 (bs, 1H, OH); 8.20 (t, J=4 Hz, 1H, NHCO); 7.05 (bs, 1H, Ph); 6.55 (bs, 2H, Ph); 4.55–4.70 (m, 1H, 5-H); 4.30–4.52 (bs, 2H, NH$_2$) 3.95 (t, J=6 Hz, 1H, 4-H); 3.60 (dd, J=7 Hz, J=4 Hz, 1H, 4-H); 3.40 lt, J=4 Hz, 2H, CH$_2$N); 1.73 (s, 3H, COCH$_3$).

The compounds listed in Table X are obtained as described for Example XXVII from the corresponding starting compounds:

TABLE X

| Ex. No. | D | Yield (% of th.) | m.p. (° C.) | $R_f$ (eluent, ratio) | $[\alpha]^{20}_D$ (DMSO) | MS (CID, NH$_3$) m/z (M + H)$^+$ |
|---|---|---|---|---|---|---|
| XXVIII | H$_2$N—/HO—CH$_3$ (aryl) | quant. | 221–222 | 0.31 (VII, 1:1) | −19.89 (c = 1.0) | 265 |

Example XXIX (5S)-3-(3-Hyrdroxy-4-(N-iso-propylamino)phenyl)-5-(acetylaminomethyl)oxazolidin-2-one

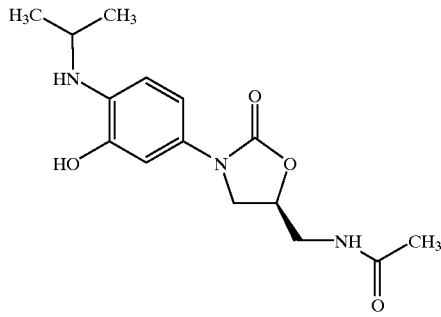

4.4 ml (4.4 mmol) of a 1 M solution of borane-tetrahydrofuran complex in THF are added at 0° C. to a mixture of 1.06 g (4.0 mmol) of the compound from Example XXVIII, 600 µl (8.0 mmol) of acetone and 50 ml of THF and the mixture is stirred at room temperature for a further 24 h. 4 ml of 1 M sodium hydroxide are added to the solution formed, the mixture is dried (Na$_2$SO$_4$) and the solvent is stripped off.

Yield: 1.23 g (quant.)

$R_f$ (I, 10:1)=0.29

MS (EI): m/z=307 (M$^+$)

$^1$H-NMR ([D$_6$] DMSO): δ=9.50 (bs, 1H, OH), 8.25 (t, 1H, NHCO), 7.10 (d, 1H, Ar-2-H), 6.62 (dd, 1H, Ar-6-H), 6.45 (d, 1H, Ar-5-H), 4.65 (m, 1H, 5-H), 3.90–4.10 (m, 2H, ArNH, 4-H), 3.50–3.70 (m, 2H, CHN, 4-H), 3.40 (t, 2H, CH$_2$N), 1.70 (s, 3H, COCH$_3$), 1.10 (d, 6H, CH$_3$).

TABLE XI

| Ex. No. | A | Yield | $R_f$ (eluent, ratio) | MS (DCI, NH$_3$) m/z (M$^+$ + H) |
|---|---|---|---|---|
| XXX | H$_3$C—CH(CH$_3$)—NH—/HO—CH$_3$ (aryl) | quant. | 0.69 (I, 5:1) | 322 |

TABLE XI-continued

![structure: A-N-oxazolidinone-CH2-NH-C(O)-CH3]

| Ex. No. | A | Yield | $R_f$ (eluent, ratio) | MS (DCI, NH$_3$) m/z (M$^+$ + H) |
|---|---|---|---|---|
| XXXI | (isopropyl-substituted)-HN-C$_6$H$_3$(OH)(CH$_3$) | quant. | 0.33 (I, 10:1) | 336 |
| XXXII | cyclopentyl-HN-C$_6$H$_3$(OH)(CH$_3$) | quant. | 0.23 (I, 10:1) | 334 |
| XXXIII | cyclobutyl-HN-C$_6$H$_3$(OH)(CH$_3$) | quant. | 0.28 (I, 10:1) | 320 |
| XXXIV | cyclopropyl-HN-C$_6$H$_3$(OH)(CH$_3$) | 8 | 0.25 (I, 10:1) | 305 |

Example XXXV (5S)-3-(2-Imino-3-methyl-2,3-dihydrobenzoxazol-6-yl)-5-acetylaminomethyl)-oxazolidin-2-one

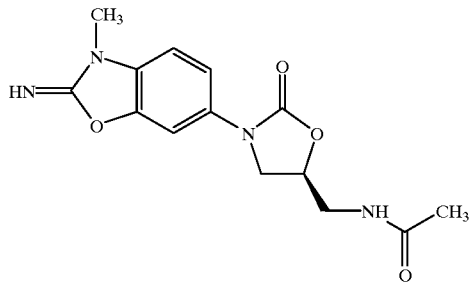

4.3 ml (69 mmol) of iodomethane are added to a solution of 2 g (6.89 mmol) of the compound from Example XXVII in 30 ml of dimethylformamide and the mixture is stirred at 100° C. for 2 h. The solvent is stripped off in vacuo and the residue is stirred in dichloromethane, filtered off with suction and dried.

Yield: 2.32 g (78%)

$R_f$ (VII, 1:1)=0.10

MS (DCI): m/z=305 (M$^+$+H)

$^1$H-NMR ([D$_6$] DMSO): δ=10.0–10.5 (bs, 1H, HN=C), 8.25 (bt, 1H, NHCO), 7.95 (d, 1H, Ar-7-H), 7.62 (d, 1H, Ar-4-H), 7.55 (dd, 1H, Ar-5-H), 4.75 (m, 1H, 5-H), 4.18 (t, 1H, 4-H), 3.78 (dd, 1H, 4-H), 3.61 (s, 3H, NCH$_3$), 3.30–3.40 (m, 2H, CH$_2$N), 1.82 (s, 3H, NCOCH$_3$).

Example XXXVI

3-Isopropyl-6-nitrobenzothiazol-2-on

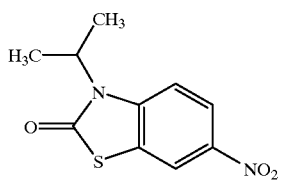

35.1 ml (0.18 mol) of 6-nitrobenzothiazol-2-on, 24.3 (0.18 mol) of potassium carbonate and 153 g (0.9 mol) of 2-isopropane in 1 l of 2-propanol are heated at reflux for 24 h. The cooled mixture is filtered, the solvent is stripped off in vacuo, the residue dissolved in dichloromethane, and washed with water. The organic phase is dried ($Na_2SO_4$), and the solvent stripped of in vacuo. The crude product obtained is chromatographed on silica gel (eluent dichloromethane/petrolether 2:1).

Yield: 8.7 g (20%)

m.p. 138–142° C.

$R_f$ (dichloromethane)=0.47

MS(CI): m/z=256 ($M+NH_4^+$)

Example XXXVII

6-Amino-3-isopropylbenzothiazol-2-on

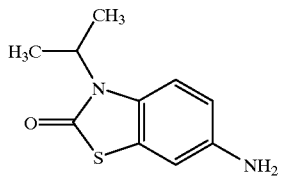

32 g (1.38 mmol) of the compound from example XXXVI are suspended in a mixture of 90 ml of ethanol, 24 ml of water and 0.96 g (8.65 mmol) of $CaCl_2$. The mixture is heated at reflux, 28.8 g (0.42 mol) of zinc-powder are added and the mixture further heated at reflux for 30 min. The reaction mixture is filtered, while hot, the precipitate washed thoroughly with water, and the ethanol is stripped off in vacuo. The residue is stirred into ether, the product is isolated by filtration and dried.

Yield: 28 g (97%)

m.p.: 138–140° C.

$R_f$ (dichloromethane)=0.19

The compounds listed in Table XII are obtained as described for Example XXXVII by reduction:

TABLE XII

A—$NH_2$

| Ex. No. | A | Yield (% of th.) | $R_f$ (eluent, ratio) |
|---|---|---|---|
| XXXVIII | ![structure] | quant. | 0.90 (VI, 10:1) |

The compound listed in Table XIII are obtained as described for Example I from the corresponding amines with benzyl chloroformate:

TABLE XIII

| Ex. No. | A | Yield (° C.) | m.p. | $R_f$ (eluent, ratio) |
|---|---|---|---|---|
| XXXIX | ![structure] | 87 | 163 | 0.15 ($CH_2Cl_2$) |
| XL | ![structure] | quant | 160 | 0.70 ($CH_2Cl_2$) |
| XLI | ![structure] | 85 | — | 0.70 (VII, 95:5) |

The compounds listed in Table XIV are obtained in analogy to the instructions of Example XXIII:

TABLE XIV

[Structure: 4-nitro-3-benzyloxyphenyl oxazolidinone with CH₂-NH-RH]

| Ex. No. | R⁴ | Acylating agent | Yield (% of th.) | R_f (eluent, ratio) | MS (CI) m/z (M + NH₄⁺) |
|---|---|---|---|---|---|
| XLII | H₃C-C(=O)- | H₃C-C(=O)-Cl | 99 | 0.36 (I, 10:1) | 417 |
| XLIII | H₃CO-C(=O)- | H₃C-O-C(=O)-Cl | 46 | 0.63 (I, 10:1) | 419 |
| XLIV | (H₃C)₃C-O-C(=O)- | BOC₂O | 95 | 0.80 (I, 10:1) | 461 |

The compounds listed in Table XV are obtained in analogy to the instructions of Example XXVII.

TABLE XV

[Structure: 4-amino-3-hydroxyphenyl oxazolidinone with CH₂-NH-R₄]

| Ex. No. | R₄ | Yield | R_f (eluent, ratio) | MS m/z |
|---|---|---|---|---|
| XLV | H₃C-C(=O)- | quant. | 0.26 (I, 10:1) | 297 (M + NH₄⁺) |
| XLVI | H₃C-O-C(=O)- | 97 | 0.40 (I, 10:1) | 299 (M + NH₄⁺) |
| XLVII | (H₃C)₃C-O-C(=O)- | quant. | 0.28 (I, 10:1) | 323 (M⁺) |

The compounds listed in Table XVI are obtained in analogy to the instructions of Example XXIX:

TABLE XVI
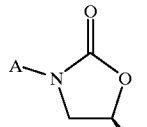
| Ex. No. | A | R | Yield (%) | $R_f$ (eluent, ratio) | MS m/z |
|---|---|---|---|---|---|
| XLVIII | 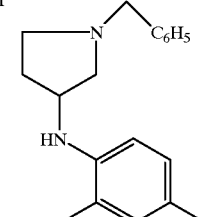 | 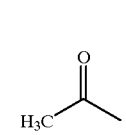 | 31 | — | — |
| XLIX | 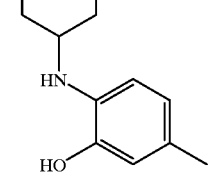 | 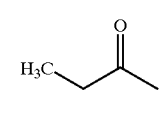 | 58 | 0.07 (I, 10:1) | 439 (M + H⁺) |
| L | 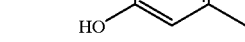 | 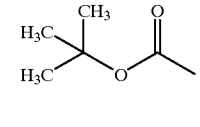 | 63 | 0.35 (I, 10:1) | 322 (M + H⁺) |
| LI |  | 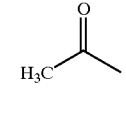 | 97 | 0.57 (I, 10:1) | — |
| LII | 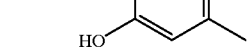 | 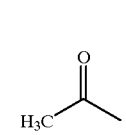 | 94 | 0.22 (I, 10:1) | 342 (M + H⁺) |

PREPARATION EXAMPLES

Example 1

(5R)-3-[3-Methyl-2-benzothiazolinon-6-yl]-(hydroxymethyl)-oxazolidin-2-one

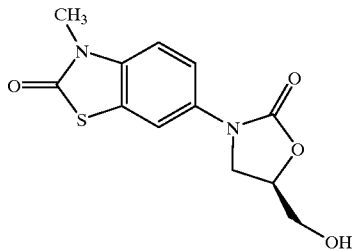

Method A

26.76 g (85.12 mmol) of the compound from Example I are dissolved in 400 ml of THF, 10 mg of 1,10-phenanthroline hydrate are added and the mixture is cooled to −70° C. Then about 34 ml of 2.5 N n-butyllithium solution in hexane are added dropwise slowly until the colour changes to red. 12 ml (85.12 mmol) of (R)-glycidyl butyrate are subsequently added dropwise. The mixture is allowed to rise to room temperature, saturated ammonium chloride solution is added, and the THF is stripped off in vacuo. The resulting precipitate is filtered off with suction, washed with water and ether and dried in a high vacuum.

Yield: 17.93 g (75%)

M.p.: 166° C.

$R_f$ (II, 1:1)=0.09

MS (EI): m/z=280 ($M^+$)

$^1$H-NMR ([$D_6$] DMSO): δ=7.80 (d, J=1 Hz, 1H, benzothiazolinone 7-H); 7.60 (dd, J=6, J=1 Hz, 1H, benzothiazolinone 5-H); 7.32 (d, J=6 Hz, 1H, benzothiazolinone 4-H); 5.23 (t, J=6 Hz, 1H, OH); 4.62–4.80 (m, 1H, 5-H); 4.10 (t, J=9 Hz, 1H, 4-H); 3.85 (dd, J=9, J=5 Hz, 1H, 4-H); 3.48–3.75 (m, 2H, $CH_2O$); 3.40 (s, 3H, $CH_3$).

Method B

9.3 g (0.03 mol) of the compound from Example I are dissolved in 150 ml of THF, and the solution is cooled to −70° C. Then 4 ml (0.01 mol) of 2.5 M n-butyllithium solution in hexane are added dropwise. Subsequently and simultaneously, a further 8 ml (0.02 mol) of n-butyllithium and 4.23 ml (0.03 mol) of (R)-glycidyl butyrate are added dropwise slowly. The mixture is allowed to warm to room temperature and is subsequently stirred for three hours. It is worked up as described for Method A. Yield: 6 g (72%).

The compounds listed in Table 1 are obtained from the corresponding carbamates as described for Example 1, Method A:

TABLE I

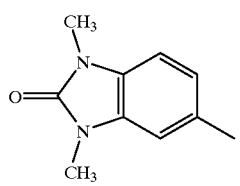

| Ex. No. | A | Yield (% of th.) | m.p. (° C.) | $R_f$ (eluent, ratio) | MS (CI) m/z ($M^+ + H$) |
|---|---|---|---|---|---|
| 2 | ![structure: 1,3-dimethyl-2-benzimidazolinon-5-yl] | 55 | 197 | 0.15 (I, 95:5) | 277 |

TABLE I-continued

![structure with A-N-oxazolidinone-CH2OH]

| Ex. No. | A | Yield (% of th.) | m.p. (° C.) | $R_f$ (eluent, ratio) | MS (CI) m/z (M+ + H) |
|---|---|---|---|---|---|
| 3 | [3-methyl-1-(3-methylbutyl)-benzimidazol-2-one-5-yl group] | 43 | 122 | 0.19 (I, 95:5) | 333 |
| 4 | [1-ethyl-3-(2-phenylethyl)-benzimidazol-2-one-5-yl group] | 72 | 149 | 0.15 (I, 95:5) | 368 |

Example 5

(5R)-3-(3-Methyl-2-benzothiazolinon-6-yl)-5-(methanesulphonyloxymethyl)-oxazolidin-2-one

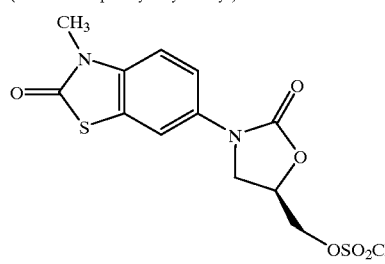

6.7 ml (86.82 mmol) of methanesulphonyl chloride are added slowly to a stirred solution, cooled to 0° C., of 18.72 g (66.78 mmol) of the compound from Example I and 13 ml (93.5 mmol) of triethylamine in 180 ml of anhydrous dichloromethane. The mixture is stirred at 0° C. for 20 min and at room temperature for a further 5 h, and the resulting precipitate is filtered off with suction, washed with water and ether and dried in a high vacuum.

Yield: 21.45 g (89%)

m.p.: 172° C.

$R_f$(I, 95:5)=0.27

MS (FAB): m/z=359 (M+)

$^1$H-NMR ([D$_6$] DMSO): δ=7.78 (d, J=1 Hz, 1H, benzothiazolinone 7-H); 7.68 (dd, J=6 Hz, J=1 Hz, 1H, benzothiazolinone 5-H); 7.35 (d, J=6 Hz, 1H, benzothiazolinone 4-H); 4.90–5.10 (m, 1H, 5-H); 4.40–4.60 (m, 2H, CH$_2$O); 4.20 (t, J=9 Hz, 1H, 4-H); 3.85 (dd, J=9 Hz, J=5 Hz, 1H, 4-H); 3.40 (s, 3H, 4-NCH$_3$); 3.20 (s, 3H, SO$_2$CH$_3$).

The methanesulphonates listed in Table 2 are obtained as described for Example 5 the corresponding alcohols.

TABLE 2

A structure: A—N(C(=O)O—CH(CH2OSO2CH3)) oxazolidinone

| Ex. No. | A | Yield (% of th.) | m.p. (° C.) | R_f (eluent, ratio) | MS (FAB) m/z (M⁺ + H) |
|---|---|---|---|---|---|
| 6 | 1,3-dimethyl-5-methyl-benzimidazol-2-one-N-yl (CH₃, CH₃) | 78 | 188 | 0.25 (I, 95:5) | 355[a] |
| 7 | 1-(3-methylbutyl)-3-methyl-5-methyl-benzimidazol-2-one-N-yl (H₃C, CH₃, CH₃) | 76 | | 0.32 (I, 95:5) | 411[a] |
| 8 | 1-ethyl-3-(2-phenylethyl)-5-methyl-benzimidazol-2-one-N-yl (C₂H₅, C₆H₅) | 67 | 187 | 0.16 (II, 1:1) | 446 |

[a] MS (EI), m/z (M)

Example 9

(5R)-3-(3-Methyl-2-benzothiazolinon-6-yl)-5-(azidomethyl)-oxazolidin-2-one

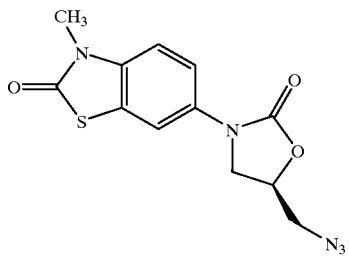

4.02 g (61.77 mmol) of sodium azide are added to a solution of 17.03 g (47.51 mmol) of the compound from Example 5 in 58 ml of anhydrous DMF, and the mixture is stirred at 70° C. for 5 h. It is cooled to room temperature and 100 ml of ice-water is stirred in. The resulting precipitate is filtered off, washed with water and petroleum ether and dried in vacuo.

Yield: 12.8 g (88%)

m.p.: 129° C.

$R_f$(I, 95:5)=0.40

MS (EI): m/z=305 (M⁺)

$^1$H-NMR ([D$_6$] DMSO): δ=7.85 (d, J=1 Hz, 1H, benzothiazolinone 7-H); 7.57 (dd, J=6 Hz, J=1 Hz, benzothiazolinone 5-H); 7.34 (d, J=6 Hz, 1H, benzothiazolinone 4-H); 4.82–5.00 (m, 1H, 5-H); 4.15 (t, J=9 Hz, 1H, 4-H); 3.65–3.77 (m, 3H, 4H, CH$_2$N$_3$); 3.41 (s, 3H, NCH$_3$).

The azides listed in Table 3 are obtained as described for Example 9 from the corresponding methanesulphonates:

TABLE 3

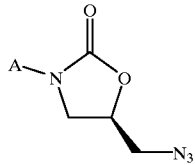

| Ex. No. | A | Yield (% of th.) | m.p. (° C.) | R_f (eluent, ratio) | MS (FAB) m/z (M+ + H) |
|---|---|---|---|---|---|
| 10 | 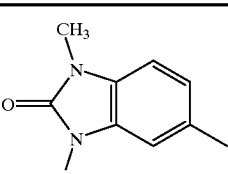 | 87 | 179 | 0.33 (I, 95:5) | 302[a] |
| 11 | | 78 | | 0.36 (I, 97:3) | 358[a] |
| 12 | | 90 | 120 | 0.51 (IV) | 393 |

[a] MS (EI), m/z (M+)

Example 13

(5S)-3-(3-Methyl-2-benzothiazolinon-6-yl)-5-(aminomethyl)-oxazolidin-2-one hydrochloride

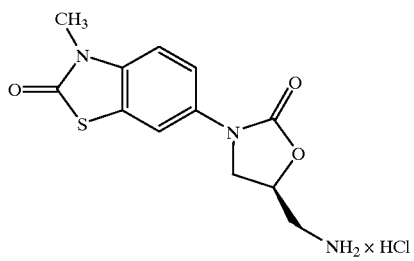

A stirred solution of 12.75 g (41.76 mmol) of the compound from Example 9 in 30 ml of 1,2-dimethoxyethane is heated to 50° C. 5.7 ml (50.11 mmol) of trimethyl phosphite are added dropwise slowly (evolution of gas) and after the addition is complete the mixture is stirred at 90° C. for 2 h. 8.4 ml of 6 N HCl are then added and stirring is continued at 90° C. for 3 h. The mixture is cooled to room temperature, and the precipitate is separated off by filtration, washed with 1,2-dimethoxyethane and dried over $P_2O_5$ in a high vacuum.

Yield: 8.86 g (75%)

m.p.: 259° C. (decomposition)

$R_f$(III, 95:5)=0.09

MS (EI): m/z=279 (M+)

$^1$H-NMR ([$D_6$] DMSO): δ=8.5 (bs, 3H, NH); 7.85 (d, J=1 Hz, 1H, benzothiazolinone 7H); 7.65 (dd, J=6 Hz, J=1 Hz, 1H, benzothiazolinone 5-H); 7.34 (d, J=6 Hz, 1H, benzothiazolinone 4-H); 4.90=5.10 (m, 1H, 5-H); 4.23 (t, J=9 Hz, 1H, 4-H); 4.42 (dd, J=9 Hz, J=5 Hz, 1H, 4-H); 3.40 (s, 3H, NCH$_3$); 3.15–3.35 (m, 2H, CH$_2$N).

The amine hydrochlorides listed in Table 4 are obtained as described for Example 13 from the corresponding azides:

TABLE 4

|  |  | Yield | m.p. | $R_f$ | MS (FAB) |
|---|---|---|---|---|---|
| Ex. No. | A | (% of th.) | (° C.) | (eluent, ratio) | m/z (M⁺ + H) |
| 14 | 1,3-dimethyl-5-methyl-benzimidazol-2-one-yl | 92 | 272 (decomp.) | 0.33 (III, 8:2) | 276[a)] |
| 15 | 1-isopentyl-3-methyl-5-methyl-benzimidazol-2-one-yl | 83 | (Oil) | 0.12 (III, 9:1) | 333 |
| 16 | 1-ethyl-3-benzyl-5-methyl-benzimidazol-2-one-yl | 95 | (Oil) | 0.5 (III, 8:2) | — |

[a)] MS (EI), m/z (M⁺)

Example 17

(5R)-3-[3-Methyl-2-benzothiazolinon-6-yl]-5-(dimethoxyphosphonamino-methyl)oxazolidin-2-one

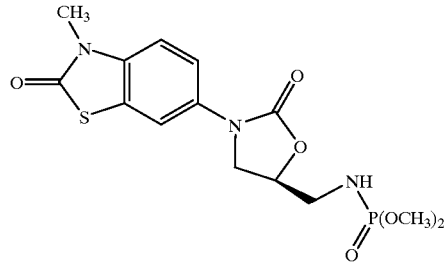

A solution of 164 mg (0.5 mmol) of the compound from Example 9 in 3 ml of 1,2-dimethoxyethane is heated to 50° C., and 0.7 ml (0.55 mmol) of trimethyl phosphite is added dropwise slowly. After the addition is complete, stirring is continued at 90° C. for a further 2 h, the solvent is subsequently stripped off and the residue is crystallized twice from ethanol.

Yield: 32 mg (20%)

m.p.: 169° C.

$R_f$(I, 95:5)=0.15

MS (FAB): m/z=388 (M⁺+H)

¹H-NMR ([D₆] DMSO): δ=7.82 (d, J=1 Hz, 1H, benzothiazolinone 7-H); 7.57 (dd, J=6 Hz, J=1 Hz, 1H, benzothiazolinone 5-H); 7.35 (d, J=6 Hz, 1H, benzothiazolinone 4-H); 5.30–5.50 (m, 1H, PNH); 4.60–4.80 (m, 1H, 5-H); 4.10 (t, J=7 Hz, 1H, 4-H); 3.90 (dd, J=7 Hz, J=4 Hz, 1H, 4-H); 3.60 (d, J=11 Hz, 3H, POCH₃); 3.55 (d, J=11 Hz, 3H, POCH₃); 3.40 (s, 3H, NCH₃).

Example 18

(5S)-3-(3-Methyl-2-benzothiazolinon-6-yl)-5-(acetylaminomethyl)oxazolidin-2-one

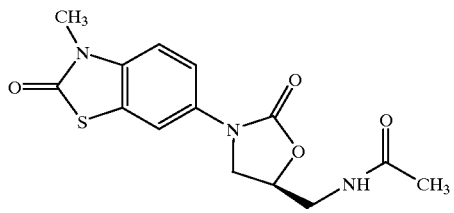

Method A

A solution of 1.09 g (27.34 mmol) of sodium hydroxide in 8 ml of water is added to a stirred solution of 8.55 g (27.07 mmol) of the compound from Example 13 in 80 ml of THF. 2.81 ml (29.78 mmol) of acetic anhydride in 6 ml of THF are added dropwise slowly thereto at 0–5° C. and the pH is kept at 9 by the simultaneous addition of a 5 N aqueous NaOH solution. Stirring is continued at 0° C. for 1 h and the THF is evaporated off in vacuo. The precipitate is filtered off with suction, washed with water and ether and dried over $P_2O_5$ in a high vacuum.

Yield: 8.39 g (96%)
m.p.: 208° C.

$R_f$(I, 95:5)=0.21

MS (DCI, $NH_3$) m/z=322 (M+H)$^+$ $^1$H-NMR ([$D_6$] DMSO): δ=8.24 (t, J=4 Hz, 1H, NH); 7.85 (d, J=1 Hz, 1H, benzothiazolinone 7-H); 7.55 (dd, J=6 Hz, J=1 Hz, 1H); benzothiazolinone 5-H); 7.32 (d, J=6 Hz, 1H, benzothiazolinone 4-H); 4.55–4.80 (m, 1H, 5-H); 4.15 (t, J=9 Hz, 1H, 4-H); 3.67 (dd, J=9 Hz, J=5 Hz, 1H, H-4); 3.35–3.50 (m, 5H, $CH_2N$, $NCH_3$); 1.83 (s, 3H, $COCH_3$).

Method B 1.10 g (2.30 mmol) of (5S)-3-(2-methylthio-3-methyl-benzo[4,5-d]-thiazol-6-yl)-5-acetylaminomethyl-oxazolidin-2-one iodide (Example XXVI) are dissolved in 24 ml of a 4:1 mixture of dichloromethane:methanol. 1.5 g of silica gel are added and the mixture is subsequently stirred at room temperature for 1 h. Then 6 ml of methanol are added and the solvent is evaporated off in vacuo. The residue is placed on a column with 100 g of silica gel and eluted with dichloromethane:methanol 95:5. The product-containing fractions are collected, the solvent is evaporated off in vacuo and the residue is recrystallized from ethanol. 343 mg (46%) of the title compound are obtained. The physical data are identical with those of the compound obtained according to Method A.

The acetamides listed in Table 5 are obtained in analogy to Example 18.

TABLE 5

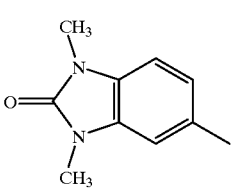

| Ex. No. | A | Method | Yield (% of th.) | m.p. (° C.) | $R_f$ (eluent, ratio) | MS (FAB) m/z (M$^+$ + H) |
|---|---|---|---|---|---|---|
| 19 | 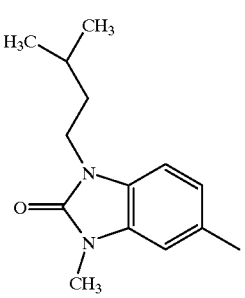 | A | 49 | 224 (decomp.) | 0.36 (I, 95:5) | 318[a)] |
| 20 | | A | 37 | 142 | 0.41 (I, 9:1) | 374[a)] |

TABLE 5-continued

| Ex. No. | A | Method | Yield (% of th.) | m.p. (° C.) | $R_f$ (eluent, ratio) | MS (FAB) m/z (M$^+$ + H) |
|---|---|---|---|---|---|---|
| 21 | ![C2H5-benzimidazolone-CH2C6H5] | A | 57 | 129–132 | 0.69 (III, 8:2) | 409 |
| 22 | ![CH3-benzothiazolone-CH2CH3] | B | 5 | / | 0.12 (I, 95:5) | 335[a] |

[a] MS (EI), m/z (M$^+$)

Example 23

(5S)-3-(1-Ethyl-2-benzimidazolon-6-yl)-5-(acetylaminomethyl)-2-oxazolidinone

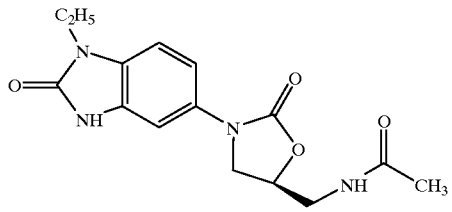

3 g (7.35 mmol) of the compound from Example 21 are initially introduced into 60 ml of NH$_3$ at −40° C. With monitoring by TLC, about 360 mg (15 mmol) of sodium are added. When conversion is complete, saturated ammonium chloride solution is added and the ammonia is evaporated off overnight. The crude product obtained is chromatographed on silica gel.

Yield: 1.5 g (64% of theory)

m.p.: 80 to 85° C.

MS (FAB): 319 (M+H$^+$)

R$_f$=0.35 (I, 9:1)

Example 24

(5S)-3-(2-Benzoxazolinon-6-yl)-5-(acetylaminomethyl)-oxazolidin-2-one

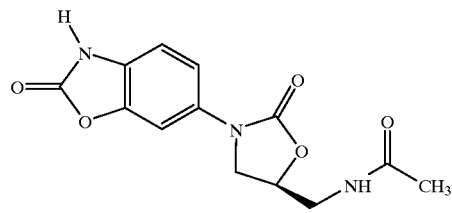

1 g (3.76 mmol) of the compound from Example XXVII and 0.67 g (4.14 mmol) of carbonyldiimidazole in 10 ml of anhydrous DMF are stirred at room temperature for 8 h. The solvent is stripped off in vacuo and the residue is stirred in dichloromethane, filtered off with suction and dried.

Yield: 0.86 g (78%)

m.p.: 219–220° C. (decomposition)

R$_f$(VII; 1:1)=0.53

$[\alpha]_D^{20}$=−23.213 (c=1.0, DMSO)

MS (FAB): m/z=292 (M$^+$+H)

$^1$H-NMR ([D$_6$] DMSO): δ=11.4–11.8 (bs, 1H, NH); 8.23 (t, J=4 Hz, 1H, NHCO); 7.55 (d, J=1 Hz, 1H, benzoxazolinone 7-H); 7.20 (dd, J=6 Hz, J=1 Hz, 1H, benzoxazolinone); 7.10 (d, J=6 Hz, 1H, benzoxazolinone 4-H); 4.60–4.80 (m, 1H, 5-H); 4.10 (t, J=6 Hz, 1H, 4-H); 3.72 (dd, J=7 Hz, J=4 Hz, 1H, 4-H); 3.40 (t, J=3 Hz, 2H, H$_2$CN); 1.82 (s, 3H, COCH$_3$).

The compounds listed in Table 6 are prepared in analogy to the instructions of Example 24:

TABLE 6

| Ex. No. | A | Yield (% of th.) | m.p. (° C.) | $R_f$ (eluent, ratio) | $[\alpha]^{20}_D$ (DMSO) | MS(FAB) m/z(M+ + H) |
|---|---|---|---|---|---|---|
| 25 | (5-methyl-benzoxazol-2(3H)-one) | 22 | 169 (Z) | 0.33 (VII, 2:1) | −16.4 (c=1) | 292 |

Example 26

(5S)-3-(2-Mercaptobenzoxazol-6-yl)-5-acetylaminomethyl)oxazolidin-2-one

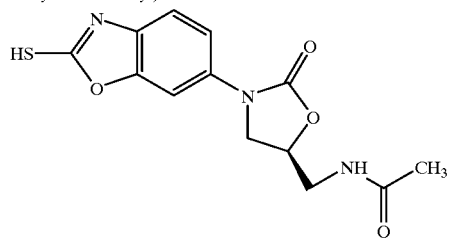

276 mg (1.04 mmol) of the compound from Example XXVIII and 184 mg (1.14 mmol) of potassium O-ethyldithiocarbonate in 6 ml of ethanol are stirred at 70° C. for 8 h. 30 ml of water and 30 ml of ethyl acetate are then added, the organic phase is separated off, the aqueous phase is extracted with ethyl acetate, the combined organic phases are washed with saturated NaCl solution and dried ($Na_2SO_4$) and the solvents are stripped off. The residue is recrystallized from methanol.

Yield: 102 mg (31%)

m.p.: 239° C. (decomposition)

$R_f$(VIII, 1:1)=0.41

$[\alpha]_D^{20}$=−25.15 (c=1.0, DMSO)

MS (CI): m/z=307 (M+)

$^1$H-NMR ([$D_6$] DMSO): δ=8.25 (t, 1H, J=4 Hz, NHCO); 7.75 (d, J=1 Hz, 1H, benzoxazole 7-H); 7.45 (dd, J=6 Hz, J=1 Hz, 1H, benzoxazole 5-H); 7.25 (d, J=6 Hz, 1H, benzoxazole 4-H); 4.65–4.82 (m, 1H, 5-H); 4.15 (t, J=6 Hz, 1H, 4-H); 3.75 (dd, J=7 Hz, 4 Hz, 1H, 4-H); 3.45 (t, J=4 Hz, 2H, $H_2$CN); 3.10–3.40 (bs, 1H); 1.85 (5, 3H, $COCH_3$).

The compounds listed in Table 7 are prepared in analogy to the instructions of Example 26:

TABLE 7

| Ex. No. | A | Yield (% of th.) | m.p. ° C. | $R_f$ (eluent, ratio) | MS(CI) m/z(M+ + H) |
|---|---|---|---|---|---|
| 27 | (HS-5-methylbenzoxazole) | 33 | >250 | 0.55 (VII, 1:1) | 307 |

Example 28

(5S)-3-(2-Mercapto-benzothiazol-6-yl)-5-(acetylaminomethyl)oxazolidin-2-one

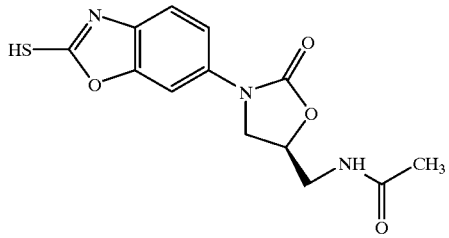

A solution of 500 mg (1.21 mmol) of (5S)-3-(2-benzylthio-benzo[4,5-d]thiazol-6-yl)-5-acetylaminomethyl-oxazolidin-2-one in 2.5 ml of trifluoroacetic acid and 0.56 ml of thioanisole is heated at 60° C. for 42 h. The mixture is allowed to cool, 25 ml of ether are added, and the precipitate is separated off by filtration, washed with 5 ml of ether and dried in a high vacuum. 59 mg (15%) of the title compound were obtained as solid.

m.p.: 161° C.

$R_f$(I, 92:8)=0.24

MS (DCI, $NH_3$): m/z=324 $(M+H)^+$ $^1$H-NMR (250 MHz, $D_6$-DMSO): δ=13.73 (bs, 1H, SH); 8.24 (m, 1H, NH); 7.86 (d, J=1 Hz, 1H, benzothiazole H-7); 7.63 (dd, J=1, 10 Hz, 1H, benzothiazole H-5); 7.30 (d, J=10 Hz, 1H, benzothiazole H-4); 4.74 (m, 1H, H-5); 4.11 (dd, J=9, 9 Hz, 1H, H-4 cis); 3.76 (dd, J=7, 9 Hz, 1H, H-4 trans); 3.42 (t, J=6 Hz, 2H, $CH_2N$); 1.84 (s, 3H, $COCH_3$).

Example 29

(5S)-3-(2-Aminobenzoxazol-6-yl)-5-(acetylaminomethyl)oxazolidin-2-one

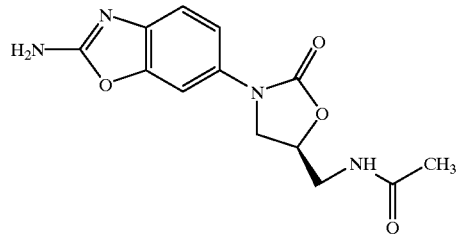

533 mg (2.19 mmol) of the compound from Example XXVIII in 10 ml of methanol are added to a solution of 253 mg (2.41 mmol) of cyanogen bromide in 2.5 ml of methanol and 2.5 ml of water, and the reaction mixture is stirred at room temperature for 20 h. The methanol is stripped off in vacuo, and the precipitate is filtered off, washed with water and dried in a high vacuum.

Yield: 393 mg (62%)

m.p.: 237° C.

$R_f$(VII, 1:1)=0.4

MS (EI): m/z=290 $(M^+)$ $^1$H-NMR ($[D_6]$ DMSO): δ=8.25 (t, J=4 Hz, 1H, NHCO); 7.62 (bs, 1H, Ph); 7.50 (bs, 2H, $NH_2$); 7.30 (bs, 1H, Ph); 7.15 (bs, 1H, 7H); 4.60–4.78 (m, 1H, 5-H); 4.12 (Z, J=7 Hz, 1H, 4-H); 3.70 (dd, J=7 Hz, J=4 Hz, 1H, 4-H); 3.35–3.45 (m, 2H, $CH_2N$); 1.80 (s, 3H, $CH_3CO$).

The compounds listed in Table 8 are prepared in analogy to Example 29:

TABLE 8

| Ex. No. | A | Yield (% of th.) | m.p. (° C.) | $R_f$ (eluent, ratio) | MS(EI) m/z $(M^+ - CI)$ |
|---|---|---|---|---|---|
| 30 | (HS-benzoxazol-5-yl) | 56 | 219–220 | 0.42 (II, 1:1) | 290 |

Example 31

(5S)-3-(2-Aminobenzoxazol-6-yl)-5-(acetylaminomethyl)oxazolidin-2-one hydrochloride

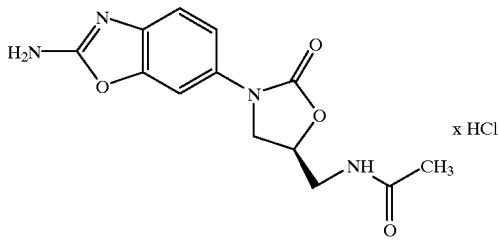

2.58 ml (2.58 mmol) of 1 N HCl in ether and then 130 ml of ether are added to a solution of 150 mg (0.52 mmol) of the compound from Example 29 in 35 ml of methanol. The precipitate is filtered off with suction, washed with ether and dried in a high vacuum.

Yield: 170 mg (89%)

m.p.: 226–227° C.

$^1$H-NMR ([D$_6$] DMSO): δ=8.8–9.2 (bs, 1H, NH); 8.28 (t, J=4 Hz, 1H, NHCO); 7.80 (s, 1H, Ph); 7.20–7.35 (m, 2H, Ph); 4.5–5.0 (m, 3H, 5-H, NH$_2$); 4.15 (t, J=7 Hz, 1H, 4-H); 3.73 (dd, J=7 Hz, J=4 Hz, 1H, 4-H); 3.40 (t, J=4 Hz, 2H, CH$_2$N); 1.80 (s, 3H, CH$_3$CO).

The compounds listed in Table 9 are prepared in analogy to Example 31:

TABLE 9

| Ex. No. | A | Yield (% of th.) | m.p. (° C.) |
|---|---|---|---|
| 32 | ![HS-benzoxazole-methyl] | 47 | 220 |

Example 33

(5S)-3-(3-Acetyl-2-benzoxazolinon-6-yl)-5-(acetylaminomethyl)oxazolidin-2-one

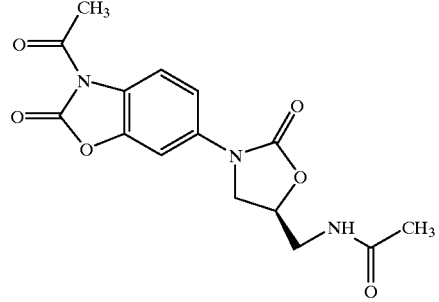

16.5 ml (0.68 mmol) of sodium hydride (80% in paraffin) are added to a solution of 200 mg (0.68 mmol) of the compound from Example 23 in 10 ml of DMF and the reaction mixture is stirred at room temperature for 15 min. Then 50 μl (54 mg, 0.68 mmol) of acetyl chloride are added dropwise at 0° C. and the mixture is stirred at 0° C. for a further 15 h. It is worked up by stripping off the solvent in vacuo, taking up the crude product in ethyl acetate and water, subjecting the aqueous phase to extraction three times with ethyl acetate, washing the combined organic phases with saturated NaCl solution, drying them (Na$_2$SO$_4$), concentrating them and recrystallizing the residue from methanol.

Yield: 54 mg (23%)

R$_f$(VII, 1:1)=0.62

MS (EI): m/z=333 (M$^+$)

$^1$H-NMR ([D$_6$] DMSO): δ=8.25 (t, J=4 Hz, 1H, NHCO); 7.90 (d, J=6 Hz, 1H, benzoxazoline 4-H); 7.72 (d, J=1 Hz, 1H, benzoxazoline 7-H); 7.33 (dd, J=6 Hz, J=1 Hz, benzoxazoline 5-H); 4.60–4.80 (m, 1H, 5-H); 4.15 (t, J=6 Hz, 1H, 4-H); 3.73 (dd, J=7 Hz, 4 Hz, 1H, 4-H); 3.55 (t, J=4 Hz, 2H, CH$_2$N); 2.60 (s, 3-H, CH$_3$CO); 1.80 (s, 3H, CH$_3$CON).

The compounds listed in Table 10 are prepared in analogy to the instructions of Example 33:

TABLE 10

| Ex. No. | A | Yield (% of th.) | m.p. (° C.) | R_f (eluent, ratio) | $[\alpha]^{20}_D$ (DMSO) | MS(FAB) m/z(M⁺ + H) |
|---|---|---|---|---|---|---|
| 34 | (6-methyl-benzoxazol-2-one, N-SO₂CH₃) | 49 | 224–225 | 0.25 (VII, 5:1) | −17.7° (c=0.5) | 370 |
| 35 | (6-methyl-benzoxazol-2-one, N-COCH₂OC₆H₅) | 54 | 220–222 | 0.26 (VII, 5:1) | −23.2° (c=0.5) | 440 |
| 36 | (6-methyl-benzoxazol-2-one, N-CO-cyclopropyl) | 82 | 223–224 | 0.36 (VII, 5:1) | −22.6° (c=0.5) | 359[a] |
| 37 | (6-methyl-benzoxazol-2-one, N-CH₃) | 53 | 243–244 | 0.20 (VII, 5:1) | −30.6° (c=0.5) | 306 |
| 38 | (6-methyl-benzoxazol-2-one, N-CH₂C₆H₅) | 77 | 247–248 | 0.29 (VII, 1:1) | −19.9° (c=0.5) | 381[a] |
| 39 | (6-methyl-benzoxazol-2-one, N-CH₂CO₂CH₂CH₃) | 57 | 197–198 | 0.22 (VII, 5:1) | −23.0° (c=0.5) | 378 |
| 40 | (6-methyl-benzoxazol-2-one, N-CH₂CN) | 29 | 210–212 | 0.25 (VII, 5:1) | −19.2° (c=1.0) | 331 |

TABLE 10-continued

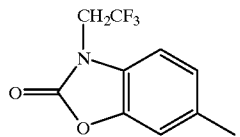

| Ex. No. | A | Yield (% of th.) | m.p. (° C.) | R_f (eluent, ratio) | $[\alpha]^{20}_D$ (DMSO) | MS(FAB) m/z(M⁺ + H) |
|---|---|---|---|---|---|---|
| 41 | 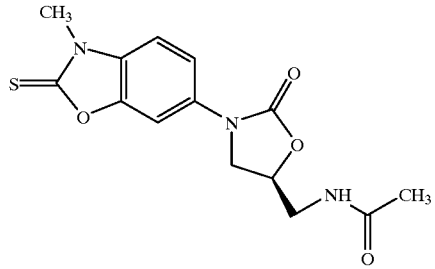 CH₂CF₃ | 82 | — | 0.60 (VII, 1:1) | — | 374 |
| 42 | 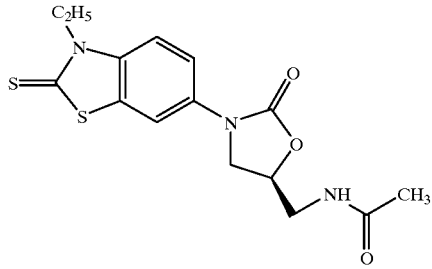 CH₂OH | 85 | 230–231 (decomp.) | 0.53 (VII, 1:1) | −20.7° (c=1.0) | 322 | a) MS(EI), m/z(M⁺)

Example 43

(5S)-3-Methyl-2-benzoxazolinethion-6-yl)-5-acetylaminomethyl)-oxazolidin-2-one

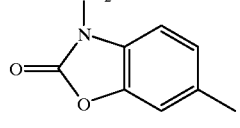

767.9 mg (2.9 mmol) of the compound from Example XXVIII and 511 mg (3.2 mol) of potassium O-ethyldithiocarbonate in 15 ml of ethanol are stirred at 70° C. for 8 h. The solvent is then stripped off, 20 ml of DMF and 410 mg (28.9 mmol) of methyl iodide are added to the residue, and the mixture is stirred at 150° C. for 20 h. It is then cooled, 40 ml of CH₂Cl₂ are added, and the precipitate is filtered off with suction, washed with CH₂Cl₂ and then boiled with methanol. The residue is dried in a high vacuum.

Yield: 602 mg (65%)

$R_f$(VII, 1:1)=0.44

MS (CI): m/z=322 (M⁺)

¹H-NMR ([D₆] DMSO): δ=8.25 (t, J=4 Hz, 1H, NHCO); 7.82 (s, 1H, Ph); 7.50 (s, 2H, Ph); 4.65–4.85 (m, 1H, 5-H); 4.15 (t, J=7 Hz, 1H, 4-H); 3.25 (dd, J=7 Hz, J=4 Hz, 1H, 4-H); 3.14 (s, 3H, NCH₃); 3.40–3.50 (m, 2H, CH₂N). 1.82 (s, 3H, CH₃CO).

Example 44

(5S)-3-(3-Ethyl-benzothioazolinethion-6-yl)-5-(acetylaminomethyl) oxazolidin-2-one 0.72 ml (9.00 mmol) of iodoethane is added to a stirred solution of 303 mg (0.90 mmol) of (5S)-3-(2-methylthio-benzo[4,5-d]thiazol-6-yl)-5-(acetylaminomethyl)-oxazolidin-2-one (Example XXVI) in 3 ml of anhydrous DMF, and the mixture is heated at 100° C. (bath temperature) for 23 h. The reaction mixture is allowed to cool, 30 ml of ether are added and the honey-like precipitate is separated off by decanting. Chromatographic purification over 58 g of silica gel (dichloromethane:methanol 95:5) gives 74 mg (25%) of the title compound as crystals.

m.p.: 224° C.

$R_f$(I, 95:5)=0.15

MS (EI): m/z=351 (M)⁺

¹H-NMR ([D₆] DMSO): δ=8.23 (m, 1H, NHCO); 7.96 (d, J=1 Hz, 1H, benzothiazolone H-7); 7.73 (dd, J=1, 9 Hz, 1H, benzothiazolone H-5); 7.63 (d, J=9 Hz, 1H, benzothiazolone H-4); 4.76 (m, 1H, H-5); 4.46 (q, J=7 Hz, 2H, CH₃CH₂); 4.17 (dd, J=10, 10 Hz, 1H, H-4 cis); 3.80 (m, 1H, H-4 cis); 3.46 (m, 2H, CH₂N); 1.83 (s, 3H, COCH₃); 1.28 (t, J=7 Hz, 3H, CH₃CH₂).

The compounds listed in Table 11 are obtained as described for Example 44:

TABLE 11

| Ex. No. | A | Yield (% of th.) | m.p. (°C.) | $R_f$ (eluent, ratio) | MS(EI) m/z (M + H⁺) |
|---|---|---|---|---|---|
| 45 | (3-propyl-6-methyl-benzothiazoline-2-thione) | 16 | 197 | 0.14 (I, 95:5) | 366 |

Example 46

(5S)-3-(3-Methyl-benzothiazolinethion-6-yl)-5-(acetylaminomethyl) oxazolidin-2-one

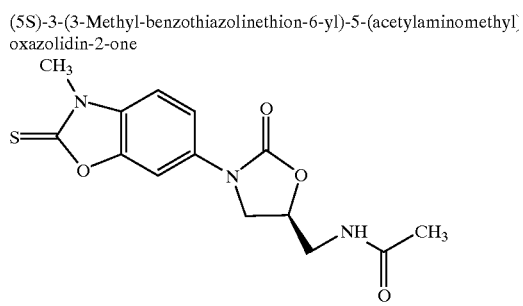

83 mg (0. 17 mmol) of the compound from Example XXVI are heated without solvent and with stirring in vacuo (1 mm) from 125° C. to 150° C. over the course of 1.5 h. The residue is allowed to cool and is washed thoroughly with 250 ml of water, stirred thoroughly with 15 ml of ethyl acetate and 5 ml of ethanol, and dried in a high vacuum over Sicapent. 48 mg (83%) of the title compound are obtained as colourless crystals.

m.p.: 253° C. (decomposition)

$R_f$(I, 95:5)=0.10

MS (FAB): m/z=338 (M+H)⁺

¹H-NMR (200 MHz, D₆-DMSO): δ=8.28 (m, 1H, NHCO); 7.91 (d, J=1 Hz, 1H, benzothiazolinethione H-7); 7.72 (dd, J=1, 9 Hz, 1H, benzothiazolinethione H-5); 7.56 (d, J=9 Hz, 1H, benzothiazolinethione H-4); 4.78 (m, 1H, H-5); 4.15 (dd, J=10, 10 Hz, 1H, H-4 cis); 3.75 (m, 4H, CH₃, H-4 trans); 3.43 (m, 2H, CH₂N); 1.85 (s, 3H, COCH₃).

The compounds listed in Table 12 are prepared in analogy to the instructions of Example 24.

TABLE 12

| Ex. No. | A | Yield | $R_f$ (eluent, ratio) | MS(DCI) m/z (M⁺ + H) |
|---|---|---|---|---|
| 47 | isopropyl-6-methyl-benzoxazol-2-one | quant. | 0.44 (I, 10:1) | 324 |
| 48 | sec-butyl-6-methyl-benzoxazol-2-one | 78 | 0.71 (I, 5:1) | 348 |
| 49 | pent-3-yl-6-methyl-benzoxazol-2-one | 73 | 0.16 (I, 10:1) | 362 |
| 50 | cyclopropyl-6-methyl-benzoxazol-2-one | 62 | 0.38 (I-10:1) | 322 |
| 51 | cyclobutyl-6-methyl-benzoxazol-2-one | 77 | 0.23 (I, 10:1) | 346 |
| 52 | cyclopentyl-6-methyl-benzoxazol-2-one | 86 | 0.22 (I, 10:1) | 360 |

The compound listed in Table 13 is prepared in analogy to the instructions of Example 33.

TABLE 13

![oxazolidinone structure with A-N group and NHC(O)CH3 side chain]

| Ex. No. | A | Yield | R_f (eluent, ratio) | MS(DCI) m/z (M+ + H) |
|---|---|---|---|---|
| 53 | ![3,5-dimethyl-benzoxazolinone] | 50 | 0.14 (VII, 5:1) | 306 |

Example 54

(5S)-3-(3-Methyl-2-benzothiazolinon-6-yl)-5-(cyclopropyl carbonylaminomethyl)-oxazolidin-2-one

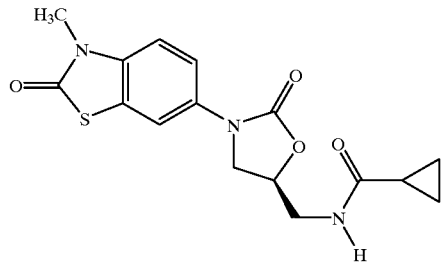

4.74 g (0.015 mol) of (5S)-3-(3-methyl-2-benzothiazolinon-6-yl)-5-(aminomethyl)oxazolidin-2-one hydrochloride (Example 13) in 150 ml of dichloromethane are placed under argon at about 5° C. 4.5 ml (0.033 mol) of triethylamine and 1.35 ml (0.015 mol) of cyclopropanecarbonyl chloride are added dropwise in succession. The mixture is stirred at room temperature for one hour, water is added, the organic phase is separated off and the solvent is stripped off. The crude product obtained is purified on silica gel (eluent: dichloromethane/methanol 100:2) and subsequently triturated with dichloromethane/petroleum ether.

Yield: 5.1 g (98%)
Melting point: 190–192° C.
R_f(I, 100:2)=0.15
MS (DCI, NH_3): m/z=348 (M+H)+

The compounds listed in Table 14 are prepared in analogy to the instructions of Example 54.

TABLE 14

![general structure: 3-methyl-benzothiazolinone linked to oxazolidinone with CH2-NH-R4]

| Ex. No. | R4 | Acylating agent | Yield (% of th.) | m.p. (° C.) | R_f (eluent, ratio) | MS(CI) m/z (M+ + H) |
|---|---|---|---|---|---|---|
| 55 | ![H-C(O)-CH3 (acetaldehyde)] | ![acetic formic anhydride] | 26 | 182–184 | 0.13 (I, 100:5) | 325[a] |
| 56 | ![H3C-C(O)-CH3 (acetone)] | ![H3C-C(O)-Cl (acetyl chloride)] | 58 | 186–188 | 0.12 (I, 100:2) | 336 |
| 57 | ![H3C-CH2-C(O)-CH3] | ![H3C-CH2-C(O)-Cl] | 76 | 185–188 | 0.25 (I, 100:5) | 350 |
| 58 | ![(H3C)2CH-C(O)-CH3] | ![(H3C)2CH-C(O)-Cl] | 79 | 218–220 | 0.29 (I, 100:5) | 350 |

TABLE 14-continued

[Structure: 3-methyl-benzothiazol-2(3H)-one linked at 6-position to an oxazolidin-2-one, with CH₂-NH-R⁴ substituent at 5-position]

| Ex. No. | R⁴ | Acylating agent | Yield (% of th.) | m.p. (°C.) | R_f (eluent, ratio) | MS(CI) m/z (M⁺ + H) |
|---|---|---|---|---|---|---|
| 59 | CH₃CH₂CH₂CH₂C(O)– | CH₃CH₂CH₂CH₂C(O)Cl | 68 | 190–192 | 0.24 (I, 100:5) | 364 |
| 60 | (CH₃)₂CHCH₂C(O)– | (CH₃)₂CHCH₂C(O)Cl | 63 | 213–215 | 0.28 (I, 100:5) | 364 |
| 61 | (CH₃)₃CC(O)– | (CH₃)₃CC(O)Cl | 69 | — | 0.15 (I, 100.5) | 364 |
| 62 | cyclobutyl-C(O)– | cyclobutyl-C(O)Cl | 74 | 195–197 | 0.20 (I, 100:5) | 379[a] |
| 63 | cyclopentyl-C(O)– | cyclopentyl-C(O)Cl | 74 | 211–213 | 0.39 (I, 100:5) | 376 |
| 64 | F₃CC(O)– | (F₃CCO)₂O | 50 | 198–200 | 0.14 (I, 100:2) | 375[b] |
| 65 | FCH₂C(O)– | FCH₂C(O)Cl | 52 | 208–210 | 0.40 (I, 100:5) | 339[b] |
| 66 | ClCH₂C(O)– | ClCH₂C(O)Cl | 45 | 192–194 | 0.48 (I, 100:5) | 373[a] |
| 67 | F₃CCH₂C(O)– | F₃CCH₂C(O)Cl | 37 | 106–108 | 0.37 (I, 100:5) | 407[a] |
| 68 | NCCH₂C(O)– | NCCH₂C(O)Cl | 29 | 113–115 | 0.10 (I, 100:2) | — |

TABLE 14-continued
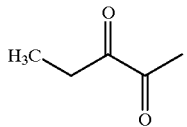
| Ex. No. | R⁴ | Acylating agent | Yield (% of th.) | m.p. (° C.) | R_f (eluent, ratio) | MS(CI) m/z (M⁺ + H) |
|---|---|---|---|---|---|---|
| 69 | 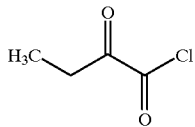 | 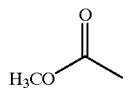 | 26 | 230–232 | 0.26 (I, 100:5) | 397[a] |
| 70 | 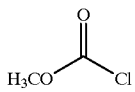 | 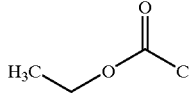 | 48 | 173–175 | 0.13 (I, 100:2) | 337[b] |
| 71 | 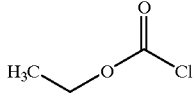 | 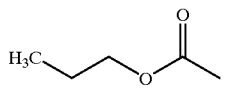 | 51 | 143–145 | 0.40 (I, 100:5) | 369[a] |
| 72 | 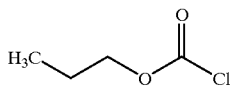 | 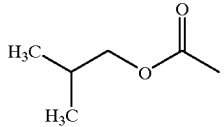 | 41 | 148–150 | 0.33 (I, 100:5) | 383[a] |
| 73 | 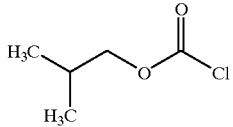 | 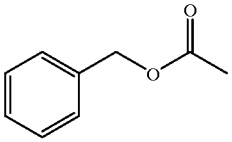 | 46 | 168–170 | 0.40 (I, 100:5) | 397[a] |
| 74 | 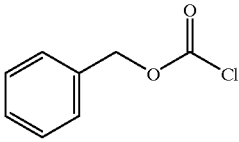 | 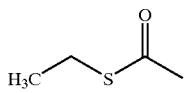 | 25 | 183–185 | 0.59 (I, 100:5) | 414 |
| 75 | 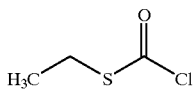 | 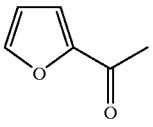 | 41 | 181–183 | 0.56 (I, 100:5) | 385[a] |
| 76 | 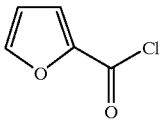 | 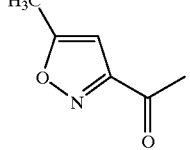 | 31 | 187–189 | 0.13 (I, 100:2) | 391[a] |
| 77 | 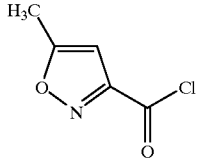 | | 49 | 228–230 | 0.25 (I, 100:2) | 406[a] |

TABLE 14-continued

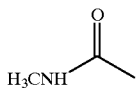

| Ex. No. | R[4] | Acylating agent | Yield (% of th.) | m.p. (° C.) | R_f (eluent, ratio) | MS(CI) m/z (M[+] + H) |
|---|---|---|---|---|---|---|
| 78 | H3CNH-C(O)- | H3C—NCO | 85 | 188–191 | 0.39 (I, 9:1) | 337 |
| 79 | H3C—SO2— | H3C—SO2Cl | 35 | 188–190 | 0.27 (I, 100:5) | 375[a] |

[a]MS(CI, NH3): m/z(M + NH4[+])
[b]MS(EI): m/z(M[+])

Example 80

(5S)-3-(3-Allyl-2-benzoxazolinon-6-yl)-5-acetylaminomethyl)oxazolidin-2-one

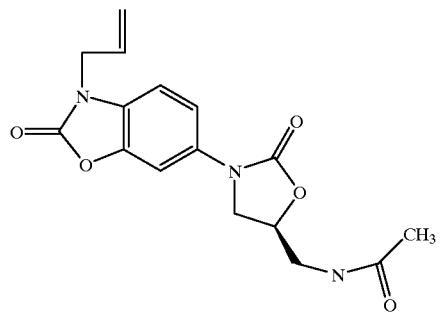

A solution of 174 mg (0.6 mmol) of the compound from Example 23 and 140 μl (0.9 mmol) of diazabicycloundecene (DBU) in 10 ml of DMF is stirred at from 40 to 50° C. for 1 h. 50 μl (0.6 mmol) of allyl bromide are then added and the mixture is stirred at 100° C. for a further 14 h. The solvent is stripped off in vacuo and the residue purified by chromatography.

Yield: 155 mg (78%)

R_f(I, 10:1)=0.33

MS (EI): m/z=331 (M[+])

$^1$H-NMR ([D_6] DMSO): δ=8.25 (bt, 1H, NHCO), 7.70 (d, 1H, benzoxazoline 7-H), 7.25 (dd, 1H, benzoxazoline 5-H), 7.15 (d, 1H, benzoxazoline 4-H), 5.80–6.05 (m, 1H, C=CH), 5.10–5.70 (m, 2H, C=CH_2), 4.80 (m, 1H, 5-H), 4.45 (d, 2H, CH_2C=C), 4.10 (t, 1H, 4-H), 3.70 (dd, 1H, 4-H), 3.40 (bt, 2H, CH_2N), 1.80 (s, 3H, COCH_3)

The compounds listed in Table 15 were prepared in analog to Example 80.

TABLE 15

| Ex. No. | A | Yield | R_f (eluent, ratio) | MS(DCI) m/z (M[+] + H) |
|---|---|---|---|---|
| 81 | 3-methyl-6-yl-2-benzoxazolinone | 49 | 0.37 (I, 10:1) | 320 |
| 82 | 3-ethyl-6-yl-2-benzoxazolinone | 69 | 0.23 (I, 10:1) | 334 |
| 83 | 3-butyl-6-yl-2-benzoxazolinone [(CH2)3—CH3] | 50 | 0.26 (I, 10:1) | 348 |

TABLE 15-continued

![structure](oxazolidinone with acetylaminomethyl)

| Ex. No. | A | Yield | $R_f$ (eluent, ratio) | MS(DCI) m/z ($M^+ + H$) |
|---|---|---|---|---|
| 84 | (CH₂)₄—CH₃ benzoxazolinone-methyl | 59 | 0.28 (I, 10:1) | 362 |
| 85 | CH₂—CH(CH₃)₂ benzoxazolinone-methyl | 24 | 0.25 (I, 10:1) | 348 |
| 86 | HOCH₂CH₂ benzoxazolinone-methyl | 51 | 0.10 (I, 10:1) | 336 |

Example 87

(5S)-3-(3-Dimethylaminomethyl-2-benzoxazolinon-6-yl)-5-(acetylaminomethyl)-oxazolidin-2-one

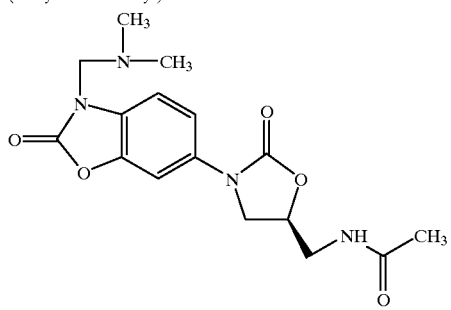

A mixture of 290 mg (1.0 mmol) of the compound from Example 23, 140 μl of a 30% formaldehyde in water, 150 μl of a 51% dimethylamine in water and 10 ml of ethanol is stirred at 80° C. for 16 h. The precipitate is filtered off at room temperature, washed with petroleum ether and dried in a high vacuum.

Yield: 86%

$R_f$(II, 5:1)=0.24

MS (DCI, NH₃): m/z=349 (M⁺+H)

¹H-NMR ([D₆] DMSO): δ=8.25 (bt, 1H, NHCO), 7.65 (d, 1H, Ar 7-H), 7.40 (d, 1H, Ar 4-H); 7.25 (dd, 1H, Ar 5-H), 4.70 (m, 1H, 5-H), 4.60 (s, 2H, NCH₂N), 4.75 (t, 1H, 4-H), 3.75 (dd, 1H, 4-H), 3.40 (t, 2H, CH₂N), 2.30 (s, 6H, NCH₃), 1.80 (s, 3H, COCH₃).

The compound listed in Table 16 is prepared analogously to Example 31.

TABLE 16

![structure with xHCl]

| Ex. No. | A | Yield (% of th.) |
|---|---|---|
| 88 | (CH₃)₂N-CH₂- on benzoxazolinone-methyl | 97 |

Example 89

(5S)-3-(2-Benzothiazolinon-6-yl)-5-(acetylaminomethyl)-oxazolidin-2-one

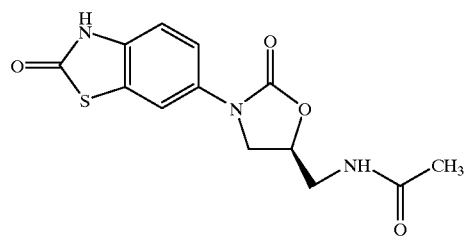

A mixture of 95 g (0.28 mol) of the compound from Example XXV and 200 g (0.37 mol) of Oxone® (potassium monopersulphate triple salt) in 5 L of water is stirred at room temperature for 24 h. 1 L of 2-propanol is added, the precipitate is filtered off with suction and the residue is purified by chromatography. 84.6 g (81%) of (5S)-3-(2-methylsulphonyl-2-benzothiazolinon-6-yl)-5-(acetylaminomethyl)-oxazolidinone are obtained. 2 g (5.4 mmol) of this compound in 50 ml of water and 10 ml of triethylamine are heated at reflux for 14 h. After the volatile constituents have been stripped off, the residue is purified by chromatography.

Yield: 1.15 g (69%)

m.p.: 223° C.

MS (CI): m/z=325 (M+NH₄⁺)

Example 90

(5S)-3-(3-Hydroxymethyl-2-benzothiazolinon-6-yl)-5-(acetylaminomethyl)-oxazolidin-2-one

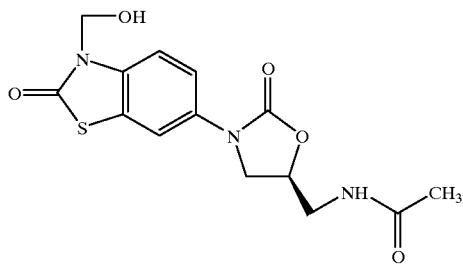

A mixture of 308 mg (1.0 mmol) of the compound from Example 89 and 0.13 ml of 37% formaldehyde solution in 1 ml of water is stirred at 70–80° C. for 14 h. The resulting precipitate is filtered off with suction, washed with water and dried.

Yield: 280 mg (83%)

m.p.: 192° C.

Example 91

(5S)-3-(3-Fluoromethyl-2-benzothiazolinon-6-yl)-5-(acetylaminomethyl)-oxazolidin-2-one

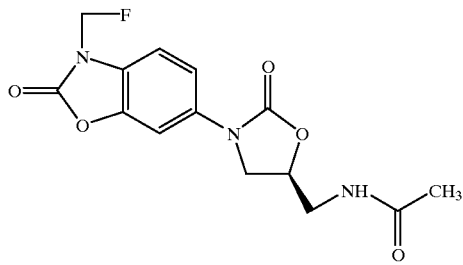

61 μl (0.466 mmol) of diethylaminosulphur trifluoride (DAST) are added at −50° C. to a suspension of 100 ml (0.311 mmol) of the compound from Example 42 and 10 ml of dichloromethane. The mixture is allowed to come to room temperature and is stirred for a further 52 h, 5 ml of saturated $NaHCO_3$ solution are added, the mixture is stirred for 10 min and then the organic phase is washed with water. The resulting precipitate is filtered off with suction, and the organic phase is dried ($Na_2SO_4$) and concentrated by evaporation.

Yield: 25 mg (25%)

$R_f$=0.22 (VII, 5:1)

MS (EI): m/z=323 (M+)

$^1$H-NMR (200 MHz, [$D_6$] DMSO): δ=8.25 (bs, 1H, NHCO), 7.72 (d, 1H, Ar-H-2), 7.55 (d, 1H, Ar-H-4), 7.32 (dd, 1H, Ar-H-5), 6.05 (d, 2H, $CH_2F$), 4.70 (m, 1H, H-5), 4.10 (t, 1H, H-4), 3.75 (d, 1H, H-4), 3.40 (m, 2H, $CH_2N$), 1.85 (s, 3H, $COCH_3$).

The compounds listed in Table 17 are obtained in analogy to the instructions of Example 91.

TABLE 17

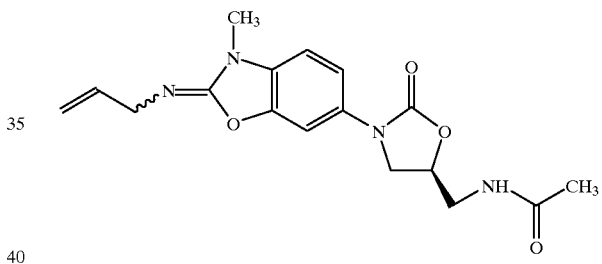

| Ex. No. | A | Yield (% of th.) | m.p. (° C.) | $R_f$ (eluent, ratio) |
|---|---|---|---|---|
| 92 | ![F-CH2-N-benzothiazolinone] | 74 | 185 | 0.54 (I, 9:1) |

Example 93

(5S)-3-(2-(Allylimino)-3-methyl-2,3-dihydrobenzoxol-6-yl)-5-(acetylaminomethyl)-oxazolidin-2-one A mixture of 0.30 g (0.694 mmol) of the compound from Example XXXV, 0.29 g (3.33 mol) of allyl bromide and 0.38 g (2.77 mmol) of anhydrous potassium carbonate in 4 ml of ethanol is heated under reflux for 11 h. For work up, the mixture is filtered with suction, the filtrate is concentrated in vacuo, and the residue is dried and purified by chromatography. The oil thus obtained is dissolved in ethyl acetate and the product is precipitated with petroleum ether.

Yield: 0.015 g (6%)

$R_f$(VII, 1:1)=0.47

MS (EI): m/z=344 (M+)

$^1$H-NMR ([$D_6$] DMSO): δ=8.24 (t, 1H, NHCO), 7.52 (d, 1H, Ar 7-H), 7.15 (dd, 1H, Ar 5-H), 7.03 (d, 1H, Ar 4-H), 5.72–6.07 (m, 1H, HC=C), 5.22 (dq, 1H, $H_2$C=C), 5.03 (dq, 1H, $H_E$C=C), 4.70 (m, 1H, 5-H), 4.10 (t, 1H, 4-H), 3.98 (m, 2H, $CH_2N$), 3.72 (dd, 1H, 4-H), 3.40 (t, 2H, $CH_2N$), 3.33 (s, 3H, $NCH_3$), 1.82 (s, 3H, $COCH_3$).

Example 94

(5S)-3-(2-Cyclopropylcarbonylimino)-3-methyl-2,3-dihydrobenzoxol-6-yl)-5-(acetylaminomethyl)-oxazolidin-2-one

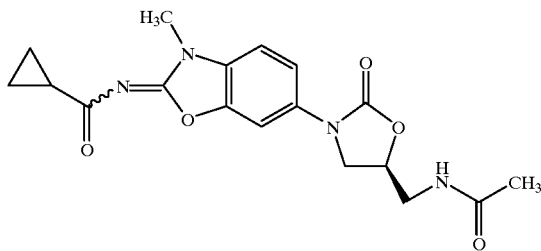

310 μl (2.2 mmol) of triethylamine are added to a suspension of 304 mg (0.703 mmol) of the compound from Example XXXV in 10 ml of THF and then 100 μl (11 mmol) of cyclopropanecarbonyl chloride are added dropwise at 0° C. After 1 h the mixture is placed in ice-water, the aqueous phase is saturated with sodium chloride, extraction with ethyl acetate is carried out three times, the extracts are dried ($Na_2SO_4$), the solvents are stripped off and the product is crystallized from dichloromethane.

Yield: 196 mg (75%)

$R_f$=0.45 (VII, 1:1)

MS (DCI/$NH_3$): m/z=373 ($M^+$+H)

$^1$H-NMR (200 MHz, [$D_6$] DMSO): δ=8.25 (bt, 1H, NHCO), 7.75 (s, 1H, Ar), 7.40 (bs, 2H, Ar), 4.75 (m, 1H, H-5), 4.15 (t, 1H, H-4), 3.40 (m, 5H, $CH_2N$, $CH_3$), 1:90 (s, 3H, $COCH_3$), 1.70 (m, 1H, Cpr-H), 0.70–0.95 (m, 4H, Cpr-H).

The compounds listed in Table 18 are prepared in analogy to the instructions of Example 94.

TABLE 18

| Ex. No. | A | Acylating agent | Yield (% of th.) | $R_f$ (eluent, ratio) | MS (CI) m/z ($M^+$ + H) |
|---|---|---|---|---|---|
| 95 | (structure) | (structure) | 79 | 0.53 (VII, 1:1) | 389 |
| 96 | (structure) | (structure) | 36 | 0.35 (VII, 1:1) | 347 |
| 97 | (structure) | (structure) | 38 | 0.53 (VII, 1:1) | 449 |
| 98 | (structure) | (structure) | 32 | 0.43 (VII, 1:1) | 439 |
| 99 | (structure) | (structure) | 62 | 0.44 (VII, 1:1) | 470 |

TABLE 18-continued

| Ex. No. | A | Acylating agent | Yield (% of th.) | R_f (eluent, ratio) | MS (CI) m/z (M⁺ + H) |
|---|---|---|---|---|---|
| 100 | H₃C—NH—C(O)—N=... (N-CH₃, benzoxazole-6-methyl) | H₃C—NCO | 46 | 0.26 (VII, 1:1) | 362 |
| 101 | NC—N=... (N-CH₃, benzoxazole-6-methyl) | BrCN | 44 | 0.37 (VII, 1:1) | 330 |

Example 102

(5S)-3-(3-Aza-1-oxa-2-thiaindan-2-dioxide-6-yl)-5-(acetylaminomethyl)-oxazolidin-2-one

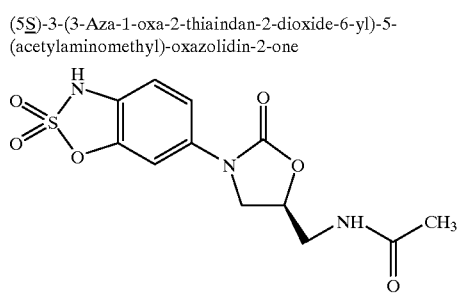

A solution of 0.17 ml (2.07 mmol) of sulphuryl chloride in 5 ml of dichloromethane is added dropwise at −5° C. to a mixture of 0.5 g (1.88 mmol) of the compound from Example 23, 0.63 ml (4.52 mmol) of triethylamine and 20 ml of anhydrous dichloromethane. The mixture is stirred at −5° C. for a further 1 h and then at room temperature for 14 h, and subsequently water is added. The aqueous phase is washed three times with dichloromethane, and the combined aqueous phases are saturated with sodium chloride and subjected four times to extraction with ethyl acetate. The ethyl acetate phases are dried (Na₂SO₄) and the solvent is stripped off in vacuo.

Yield: 98 mg (16%)

R_f(VII, 1:1)=0.17

MS (FAB): m/z=326 (M⁺-H)

¹H-NMR ([D₆] DMSO): δ=8.25 (t, 1H, NHCO), 7.50 (d, 1H, Ar 7-H), 7.27 (dd, 1H, Ar 5-H), 7.05 (d, 1H, Ar 4-H), 4.70 (m, 1H, 5-H), 4.05 (t, 1H, 4-H), 3.65 (dd, 1H, 4-H), 3.40 (t, 1H, CH₂N), 1.80 (s, 3H, COCH₃).

The compounds listed in Table 19 are obtained in analogy to the instructions of Example 1:

TABLE 19

[Structure: A—N-oxazolidinone-CH2-OH]

| Ex. No. | A | Yield (% of theory) | m.p. (° C.) | R_f (eluent, ratio) | MS m/z |
|---|---|---|---|---|---|
| 103 | [6-methyl-benzothiazol-2(3H)-one-N-CH2-] | 76 | 156 | 0.32 (I, 100:5) | 312 (M + NH$_4^+$) |
| 104 | [6-methyl-benzothiazol-2(3H)-one-N-CH(CH3)2-] | 62 | 157 | 0.33 (I, 10:5) | 326 (M + NH$_4^+$) |
| 105 | [6-methyl-benzoxazol-2(3H)-one-N-CH2-] | 50 | — | 0.12 (II, 1:1) | 296 (M + NH$_4^+$) |

The compounds listed in Table 20 are obtained in analogy to the instructions of Example 5:

TABLE 20

[Structure: A-substituted γ-butyrolactone-CH2-OSO2CH3]

| Ex. No. | A | Yield (% of theory) | m.p. (° C.) | R_f (eluent, ratio) | MS m/z |
|---|---|---|---|---|---|
| 106 | [6-methyl-benzothiazol-2(3H)-one-N-CH2-] | 86 | 150 | 0.52 (I, 100:5) | — |
| 107 | [6-methyl-benzothiazol-2(3H)-one-N-CH(CH3)2-] | quant | — | 0.58 (I, 100:5) | — |

TABLE 20-continued

[Structure: tetrahydrofuran-2-one with A substituent at 3-position and -OSO₂CH₃ group at 5-position]

| Ex. No. | A | Yield (% of theory) | m.p. (° C.) | R_f (eluent, ratio) | MS m/z |
|---|---|---|---|---|---|
| 108 | [6-methyl-3-ethyl-benzoxazol-2(3H)-one] | 95 | — | 0.31 (VII, 5:1) | 357 (M + NH₄⁺) |

The compounds listed in Table 21 are obtained in analogy to the instructions of Example 9:

TABLE 21

[Structure: oxazolidin-2-one with A substituent on N and -N₃ group at 5-position methyl]

| Ex. No. | A | Yield (% of theory) | m.p. (° C.) | R_f (eluent, ratio) | MS m/Z |
|---|---|---|---|---|---|
| 109 | [6-methyl-3-ethyl-benzothiazol-2(3H)-one] | 93 | 180–183 | 0.69 (I, 100:5) | — |
| 110 | [6-methyl-3-isopropyl-benzothiazol-2(3H)-one] | 91 | — | 0.69 (I, 100:5) | — |
| 111 | [6-methyl-3-ethyl-benzoxazol-2(3H)-one] | 88 | — | 0.27 (VII, 5:1) | 304 (M + H⁺) |

The compounds listed in Table 22 are obtained in analogy to the instructions of Example 13:

TABLE 22

Structure: A—N-oxazolidinone-CH2-NH2 × HCl

| Ex. No. | A | Yield (% of theory) | m.p. (° C.) | R_f (eluent, ratio) | MS m/Z |
|---|---|---|---|---|---|
| 112 | 6-methyl-benzothiazol-2(3H)-one-N-CH2- (with CH3) | 91 | 258 (dec) | 0.25 (I, 9:1) | 311 (M + NH$_4^+$) |
| 113 | 6-methyl-benzothiazol-2(3H)-one-N-CH(CH3)2 | 90 | 231 (dec) | 0.19 (I, 9:1) | 325 (M + NH$_4^+$) |
| 114[a)] | 6-methyl-benzoxazol-2(3H)-one-N-CH2- (with CH3) | quant | — | 0.21 (I, 10:1) | 295 (M + NH$_4^+$) |

[a)] isolated as free amine in analogy to the instructions of Example XXVII

The compounds listed in Table 23 are obtained in analogy to the instructions of Example 54:

TABLE 23

Structure: A—N-oxazolidinone-CH2-NH—R4

| Ex. No. | A | R4 | Yield (%) | m.p. (° C.) | R_f (eluent, ratio) | MS m/Z |
|---|---|---|---|---|---|---|
| 115 | 6-methyl-benzothiazol-2(3H)-one-N-CH2- | H3C-C(=O)-CH2-C(CH3)- | 73 | 175 | 0.26 (I, 100:5) | 350 |
| 116 | 6-methyl-benzothiazol-2(3H)-one-N-CH2- | cyclopropyl-C(=O)-CH2- | 74 | 191 | 0.28 (I, 100:5) | 362 (M + H$^+$) |

TABLE 23-continued

[Structure: oxazolidinone with A-N and CH2-NH-R4 substituents]

| Ex. No. | A | R4 | Yield (%) | m.p. (° C.) | R<sub>f</sub> (eluent, ratio) | MS m/Z |
|---|---|---|---|---|---|---|
| 117 | 3-ethyl-6-methyl-benzothiazol-2(3H)-one | methoxycarbonyl (H3CO-C(=O)-) | 55 | 142 | 0.50 (I, 100:5) | 352 (M + H$^+$) |
| 118 | 3-ethyl-6-methyl-benzothiazol-2(3H)-one | ethoxycarbonyl (H3C-CH2-O-C(=O)-) | 51 | 129 | 0.45 (I, 100:5) | 383 (M + H$^+$) |
| 119 | 3-isopropyl-6-methyl-benzothiazol-2(3H)-one | acetyl (H3C-C(=O)-) | 64 | 132 | 0.20 (I, 100:5) | 367 (M + H$^+$) |
| 120 | 3-isopropyl-6-methyl-benzothiazol-2(3H)-one | propionyl (H3C-CH2-C(=O)-) | 69 | 143 | 0.35 (I, 100:5) | 363 (M$^+$) |
| 121 | 3-isopropyl-6-methyl-benzothiazol-2(3H)-one | cyclopropylcarbonyl | 57 | 143 | 0.38 (I, 100:5) | 375 (M$^+$) |
| 122 | 3-isopropyl-6-methyl-benzothiazol-2(3H)-one | methoxycarbonyl (H3C-O-C(=O)-) | 64 | 151 | 0.39 (I, 100:5) | 383 (M + NH$_4^+$) |
| 123 | 3-methyl-6-methyl-benzoxazol-2(3H)-one | methoxycarbonyl (H3C-O-C(=O)-) | 53 | — | 0.40 (I, 10:1) | 339 (M + H$^+$) |

TABLE 23-continued

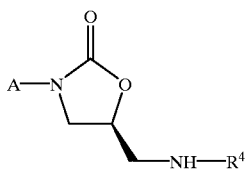

| Ex. No. | A | R[4] | Yield (%) | m.p. (° C.) | $R_f$ (eluent, ratio) | MS m/Z |
|---|---|---|---|---|---|---|
| 124 | 3-ethyl-6-methyl-benzoxazol-2(3H)-one | cyclopropyl C(=O)- | 69 | — | 0.46 (I, 10:1) | 346 (M + H[+]) |
| 125 | 3-ethyl-6-methyl-benzoxazol-2(3H)-one | CH3O-C(=O)- | 48 | — | 0.43 (I, 10:1) | 353 (M + H[+]) |
| 126 | 3-isopropyl-6-methyl-benzoxazol-2(3H)-one | CH3-C(=O)- | 82 | — | 0.44 (I, 10:1) | 334 (M + H[+]) |
| 127 | 3-isopropyl-6-methyl-benzoxazol-2(3H)-one | CH2=CH-C(=O)- | 90 | — | 0.45 (I, 10:1) | 348 (M + H[+]) |
| 128 | 3-isopropyl-6-methyl-benzoxazol-2(3H)-one | cyclopropyl-C(=O)- | 86 | — | 0.45 (I, 10:1) | 360 (M + H[+]) |
| 129 | 3-isopropyl-6-methyl-benzoxazol-2(3H)-one | CH3O-C(=O)- | 85 | — | 0.49 (I, 10:1) | 350 (M + H[+]) |
| 130 | 3-isopropyl-6-methyl-benzoxazol-2(3H)-one | C6H5CH2O-C(=O)- | 48 | — | 0.71 (I, 10:1) | 443 (M + NH4[+]) |

TABLE 23-continued

[Structure: A—N-oxazolidinone-CH2-NH—R⁴]

| Ex. No. | A | R⁴ | Yield (%) | m.p. (° C.) | R_f (eluent, ratio) | MS m/Z |
|---|---|---|---|---|---|---|
| 131[a] | 3-methyl-6-methyl-benzothiazol-2(3H)-one | F-cyclopropyl-C(O)- (rac) | 57 | — | 0.26 (I, 100:5) | 366 (M + H⁺) |
| 132[a] | 3-methyl-6-methyl-benzothiazol-2(3H)-one | F-cyclopropyl-C(O)- (rac) | 56 | — | 0.31 (I, 100:5) | 366 (M + H⁺) |
| 133[a] | 3-ethyl-6-methyl-benzothiazol-2(3H)-one | C(O)-cyclopropyl-F (rac) | 37 | 209 | 0.37 (I, 100:5) | 397 (M + NH₄⁺) |
| 134[a] | 3-ethyl-6-methyl-benzothiazol-2(3H)-one | C(O)-cyclopropyl-F (rac) | 72 | 182 | 0.34 (I, 100:5) | 397 (M + NH₄⁺) |

[a]prepared from the corresponding carboxylic acids with 1-hydroxybenzotriazol (HOBT)/N-ethyl-N-(3-dimethylamino) carbodiimide (EDC)

The compounds listed in Table 24 are obtained in analogy to the instructions of Example 24:

TABLE 24

[Structure: A—N-oxazolidinone-CH2-NH—R⁴]

| Ex. No. | A | R⁴ | Yield (% of theory) | R_f (eluent, ratio) | MS m/Z |
|---|---|---|---|---|---|
| 135 | 3-(1-chloromethyl-ethyl)-6-methyl-benzoxazol-2(3H)-one | H₃C-C(O)- | 65 | 0.29 (I, 10:1) | 368 (M + H⁺) |

TABLE 24-continued

| Ex. No. | A | R⁴ | Yield (% of theory) | $R_f$ (eluent, ratio) | MS m/Z |
|---|---|---|---|---|---|
| 136 | (1-benzylpyrrolidin-3-yl on 6-methyl benzoxazolone) | acetone | 93 | 0.44 (I, 10:1) | — |
| 137 | (1-benzylpiperidin-4-yl on 6-methyl benzoxazolone) | acetone | quant | 0.13 (I, 10:1) | 465 (M + H⁺) |
| 138 | (H on 6-methyl benzoxazolone) | 2-butanone | 79 | 0.26 (I, 10:1) | 323 (M + NH₄⁺) |
| 139 | (isopropyl on 6-methyl benzoxazolone) | tert-butyl acetate | 96 | 0.71 (I, 10:1) | 409 (M + NH₄⁺) |
| 140 | (H on 6-methyl benzoxazolone) | tert-butyl acetate | 49 | 0.34 (I, 10:1) | 367 (M + NH₄⁺) |
| 141 | (H on 6-methyl benzoxazolone) | methyl acetate | 66 | — | 325 (M + NH₄⁺) |
| 142 | (isopropyl on 6-methyl benzoxazolone) | 2-butanone | 82 | 0.38 (I, 10:1) | 348 (M + H⁺) |

The compounds listed in Table 25 are obtained in analogy to the instructions of Example 80:

TABLE 25

| Ex. No. | A | R⁴ | Yield (% of theory) | $R_f$ (eluent, ratio) | MS m/Z |
|---|---|---|---|---|---|
| 143 | 4-pyridylmethyl-substituted 6-methyl-benzoxazolone | acetone (H₃C-CO-CH₃) | 65 | 0.32 (I, 10:1) | 397 (M + H⁺) |
| 144 | N-CH₃ 6-methyl-benzoxazolone | H₃C-CO-CH₂CH₃ | 74 | 0.52 (I, 10:1) | 337 (M + H⁺) |
| 145 | N-CH₂CH₃ 6-methyl-benzoxazolone | H₃C-CO-CH₂CH₃ | 64 | 0.37 (I, 10:1) | 351 (M + NH₄⁺) |
| 146 | N-(CH₂)₂CH₃ 6-methyl-benzoxazolone | H₃C-CO-CH₂CH₃ | 85 | 0.32 (I, 10:1) | 365 (M + NH₄⁺) |
| 147 | N-CH₂-CH(CH₃)₂ 6-methyl-benzoxazolone | H₃C-CO-CH₂CH₃ | 36 | — | 379 (M + NH₄⁺) |
| 148 | N-CH₂-C(O)-O-CH₂-C₆H₅ 6-methyl-benzoxazolone | H₃C-CO-CH₂CH₃ | 76 | 0.81 (I, 10:1) | 454 (M + H⁺) |
| 149 | N-(CH₂)₂-phthalimidyl 6-methyl-benzoxazolone | H₃C-CO-CH₂CH₃ | 41 | 0.31 (I, 10:1) | 496 (M + H⁺) |

TABLE 25-continued

| Ex. No. | A | R⁴ | Yield (% of theory) | R_f (eluent, ratio) | MS m/Z |
|---|---|---|---|---|---|
| 150 | 6-methyl-3-(3-phthalimidopropyl)-benzoxazol-2(3H)-one | propanoyl | 73 | 0.30 (I, 10:1) | 493 (M + H⁺) |
| 151 | 3,6-dimethyl-benzoxazol-2(3H)-one | methoxycarbonyl | 90 | 0.43 (I, 10:1) | 353 (M + H⁺) |
| 152 | 3,6-dimethyl-benzoxazol-2(3H)-one | tert-butoxycarbonyl | 23 | 0.49 (I, 10:1) | 381 (M + H⁺) |
| 153 | 3,6-dimethyl-benzoxazol-2(3H)-one | tert-butoxycarbonyl | 63 | 0.48 (I, 10:1) | 395 (M + NH₄⁺) |

The compounds listed in Table 26 are obtained in analogy to the instructions of Example V:

TABLE 26

| Ex. No. | A | R⁴ | Yield (% of theory) | m.p. (° C.) | R_f (eluent, ratio) | MS m/Z |
|---|---|---|---|---|---|---|
| 154 | 3,6-dimethyl-benzothiazol-2(3H)-one | acetyl | 31 | 166 | 0.61 (I, 9:1) | 353 (M + NH₄⁺) |

TABLE 26-continued
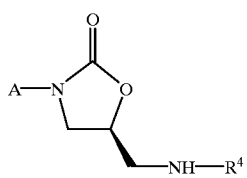
| Ex. No. | A | R⁴ | Yield (% of theory) | m.p. (° C.) | $R_f$ (eluent, ratio) | MS m/Z |
|---|---|---|---|---|---|---|
| 155 | 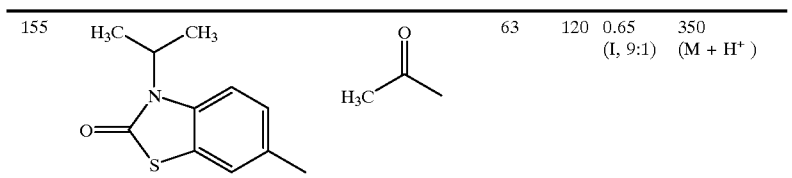 | | 63 | 120 | 0.65 (I, 9:1) | 350 (M + H⁺) |
The compounds listed in Table 27 are obtained in analogy to the instructions of Example 31 using 4NHCl in dioxan:
TABLE 27
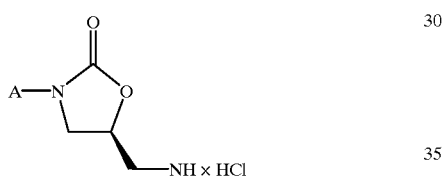
| Ex. No. | A | Yield (% of theory) | MS m/Z |
|---|---|---|---|
| 156 | 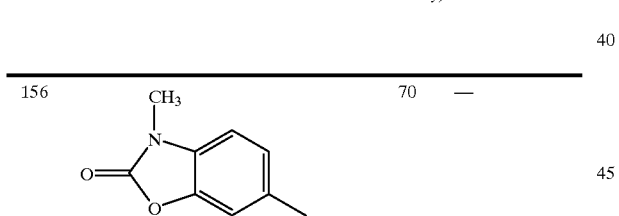 | 70 | — |
| 157 | 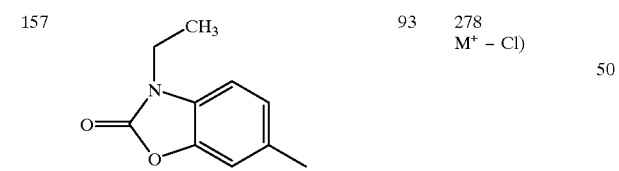 | 93 | 278 (M⁺ − Cl) |
| 158 | 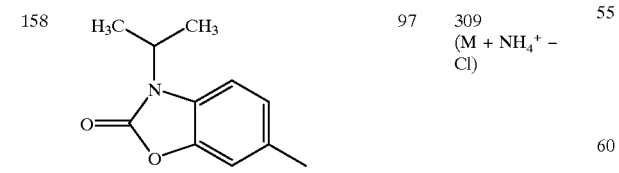 | 97 | 309 (M + NH₄⁺ − Cl) |
The compounds listed in Table 28 are obtained in analogy to the instructions of Example 9.

TABLE 28

| Ex. No. | A | R⁴ | Yield (% of theory) | $R_f$ (eluent, ratio) | MS m/Z |
|---|---|---|---|---|---|
| 159 | H₃C—CH(—N₃)—CH₂— attached to N of 6-methyl-benzoxazolin-2(3H)-one | H₃C—C(=O)— | 95 | 0.29 (I, 10:1) | 392 (M + $NH_4^+$) |

Example 160

(5S)-3-(3-Aminopropyl)2-benzoxazolinon-6-yl)-5-(propionylaminomethyl)-2-oxazolidinone

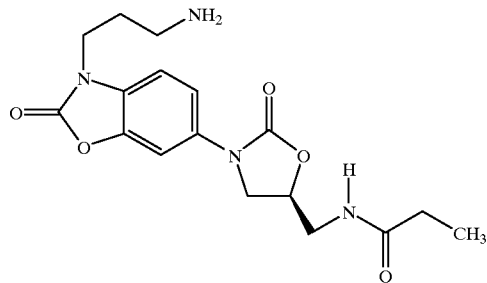

320 μl (4.1 mmol) of 40% methylamin in water are added to a suspension of 328 mg (0.67 mmol) of the compound of Example 150 and 20 ml of ethanol, and the mixture is stirred for 3 h at 70° C. and for 1 h at reflux. The precipitate is filtered off with suction, washed with ethanol and dried.

Yield: 123 mg (51%)

$R_f$(I, 10:1)=0.21

¹H-NMR (200 MHz, [D₆]DMSO): δ=8.10 (bt, 1H, NH), 7.18 (d, 1H, Ar—H), 7.08 (d, 1H, Ar—H), 6.81 (dd, 1H, Ar—H), 6.60 (bs, 2H, $NH_2$), 4.70 (m, 1H, 5-H), 4.10 (t, 1H, 4-H), 3.70 (dd, 1H, 4-H), 3.40 (m, 4H, $CH_2N$), 3.20 (m, 2H, $CH_2N$), 2.10 (q, 2H, $COCH_2$), 1.90 (m, 2H, $CH_2$), 0.95 (t, 3H, $CH_3$).

The compounds listed in Table 29 are obtained in analogy to the instructions of Example 160.

TABLE 29

| Ex. No. | A | Yield (% of theory) | $R_f$ (eluent, ratio) | MS m/Z |
|---|---|---|---|---|
| 161 | H₂N—(CH₂)₂— attached to N of 6-methyl-benzoxazolin-2(3H)-one | 17 | 0.30 (I, 10:1) | 347 (M + $H^+$) |

The compounds listed in Table 30 are obtained in analogy to the instructions of Example XXVII:

TABLE 30

![Structure: A-N-oxazolidinone-CH2-NH-R4]

| Ex. No. | A | R⁴ | Yield (% of theory) | R_f (eluent, solvent) | MS m/Z |
|---|---|---|---|---|---|
| 162 | 4-(6-methyl-2-oxo-benzoxazol-3-yl)piperidin-1-yl (NH) | acetyl (H₃C-C(O)-) | 13 | 0.01 (I, 10:1) | 375 (M + H⁺) |
| 163 | (6-methyl-2-oxo-benzoxazol-3-yl)-CH₂-CO₂H | acetyl | 32 | 0.01 (I, 10:1) | 364 (M + H⁺) |
| 164 | H₃C-CH(-)-CH₂-N(6-methyl-2-oxo-benzoxazol-3-yl), NH₂ | acetyl | quant | 0.11 (I, 100:1) | — |

The compounds listed in Table 31 are obtained in analogy to the instructions of Example 31:

TABLE 31

![Structure: A-N-oxazolidinone-CH2-NH-R4]

| Ex. No. | A | R⁴ | Yield (% of theory) | MS m/Z |
|---|---|---|---|---|
| 165 | H₃C-CH(-)-CH₂-NH₂ × HCl, N-(6-methyl-2-oxo-benzoxazol-3-yl) | acetyl | 25 | — |
| 166 | (CH₂)₃—NH₂ × HCl on N-(6-methyl-2-oxo-benzoxazol-3-yl) | H₃C-C(O)-CH₂- (propionyl) | 60 | 363 (M + H⁺) |

TABLE 31-continued

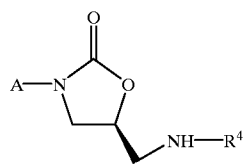

| Ex. No. | A | R[4] | Yield (% of theory) | MS m/Z |
|---|---|---|---|---|
| 167 | 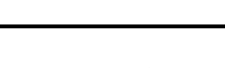 | 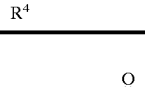 | 31 | — |

The compounds listed in Table 32 are obtained in analogy to the instructions of Example 33:

TABLE 32

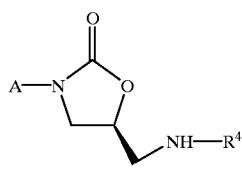

| Ex. No. | A | R | Yield (% of theory) | $R_f$ (eluent, ratio) | MS m/Z |
|---|---|---|---|---|---|
| 168 | 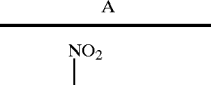 | 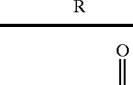 | 43 | 0.55 (I, 10:1) | 445 M + $NH_4{}^*$) |

What is claimed is:
1. Compounds of the formula (I):

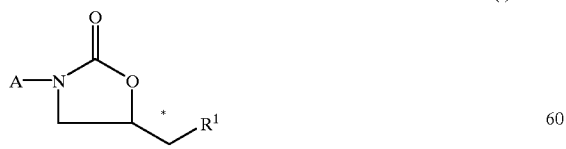

in which $R^1$ represents azido, hydroxyl or represents a group of the formula —$OR^2$, —O—$SO_2R^3$ or —$NR^4R^5$, in which
$R^2$ denotes straight-chain or branched acyl having up to 8 carbon atoms, or a hydroxy-protecting group, $R^3$ denotes straight-chain or branched alkyl having up to 4 carbon atoms or phenyl or tolyl, $R^4$ and $R^5$ are identical or different and denote cycloalkyl having 3 to 6 carbon atoms, hydrogen, phenyl or straight-chain or branched alkyl or alkoxy having in each case up to 8 carbon atoms, or an amino-protecting group, or $R^4$ and $R^5$ denotes a group of the formula —CO—$R^6$, $P(O)(OR^7)(OR^8)$ or —$SO_2$—$R^9$, in which $R^6$ denotes cycloalkyl or halogen substituted cycloalkyl each having 3 to 6 carbon atoms, straight-chain or branched alkoxy having up to 8 carbon atoms, phenyl, benzyloxy or hydrogen, or $R^6$ denotes straight-chain or branched alkyl or alkenyl each having up to 8 carbon atoms which are optionally substituted by cyano or halogen, or $R^6$ denotes straight-chain or branched thioalkyl or acyl having in each case up to 6 carbon atoms, or R[6] denotes a group of the formula —NR[10]R[11], in which
R[10] and R[11] are identical or different and denote hydrogen, phenyl or straight-chain or branched alkyl having up to 6 carbon atoms, or
R[6] denotes isoxazolyl, furyl, thienyl, pyrroyl, oxazolyl or imidazolyl, each of which is optionally substituted by straight-chain or branched alkyl having up to 3 carbon atoms,
R[7] and R[8] are identical or different and denote hydrogen or straight-chain or branched alkyl having up to 4 carbon atoms,
R[9] denotes straight-chain or branched alkyl having up to 4 carbon atoms, or phenyl,
A represents a radical of the formula:

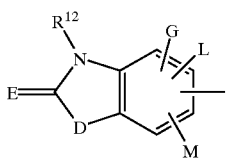

in which
G, L and M are identical or different and represent hydrogen, carboxyl, fluorine, chlorine, cyano, formyl, trifluromethyl, straight-chain or branched alkyl having up to 3 carbon atoms, or a group of the formula —CO—NR[17]R[18], in which
R[17] and R[18] are identical or different and denote hydrogen, straight-chain or branched alkyl having up to 4 carbon atoms, or phenyl,
R[12] denotes cycloalkylcarbonyl or cycloalkyl having in each case 3 to 6 carbon atoms, or denotes straight-chain or branched alkoxycarbonyl having up to 6 carbon atoms, or denotes straight-chain or branched alkyl or alkenyl having in each case up to 10 carbon atoms, which are optionally substituted by cyano, azido, halogen, hydroxyl, carboxyl, straight-chain or branched alkoxycarbonyl having up to 6 carbon atoms, benzloxycarbonyl, aryl having 6 to 10 carbon atoms, cycloalkyl having 3 to 6 carbon atoms or by a group of the formula —(CO)$_c$—NR[19]R[20], —N(R[21])—SO$_2$—R[22], R[23]R[24]—N—SO$_2$—, R[25]—S(O)$_d$— or

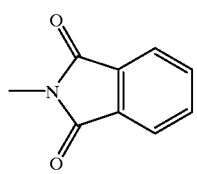

in which
c is a number 0 or 1,
R[19], R[20] and R[21] have the meaning given above of R[17] and R[18] and are identical to or different from it, or together with the nitrogen atom form a 5-membered saturated heterocycle having optionally a further heteroatom selected from the group consisting of N, S or O, which can in turn optionally be substituted, even on a further nitrogen atom, by straight-chain or branched alkyl or acyl having up to 3 carbon atoms,
R[23] and R[24] have the meaning given above of R[17] and R[18] and are identical to or different from it,
d denotes a number 0, 1 or 2, R[22] and R[25] are identical or different and denote straight-chain or branched alkyl having up to 4 carbon atoms, benzyl, phenyl or tolyl, or
R[12] denotes a residue of a formula:

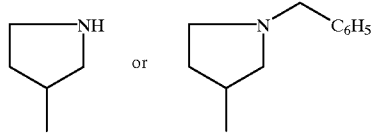

R[12] denotes a group of the formula —COCCl$_3$ or straight-chain or branched acyl having up to 6 carbon atoms which is optionally substituted by trifluoromethyl, trichloromethyl or by a group of the formula —OR[26], in which
R[26] denotes hydrogen or straight-chain or branched alkyl having up to 6 carbon atoms which is optionally substituted by aryl having up to 10 carbon atoms,
R[12] denotes a group of the formula —(CO)$_e$—NR[27]R[28], —NR[29]—SO$_2$R[30], R[31]R[32]—N—SO$_2$— or R[33]—S(O)$_f$, in which
e has the meaning given above of c and is identical to or different from it,
R[27] and R[28] and R[29] each have the meaning given above of R[19], R[20] and R[21] and are identical to or different from it,
R[31] and R[32] have the meaning given above of R[17] and R[18] and are identical to or different from it,
f has the meaning given above of d and is identical to or different from it,
R[30] and R[33] have the meanings in each case given above of R[22] and R[25] and are identical to or different from these,
D denotes a sulphur atom or an oxygen atom,
E denotes an oxygen or sulphur atom,
and the tautomeric forms, isomers and salts thereof.

2. Compounds according to claim 1, characterized in that

G, L and M represent hydrogen and the oxazolidinone radical is attached in positions 5 or 6 to the phenyl ring.

3. The compound according to claim 1, which has the formula:

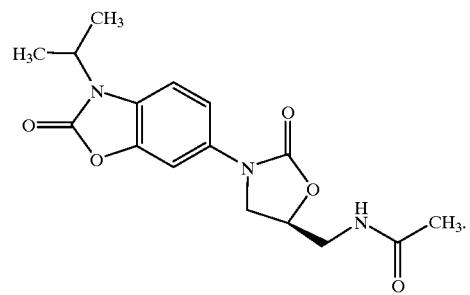

4. The compound according to claim 1, which has the formula

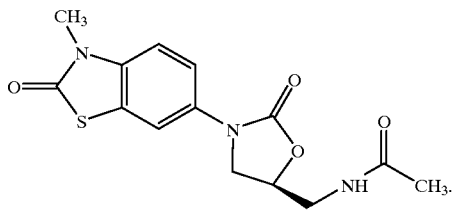

5. The compound according to claim 1, which has the formula

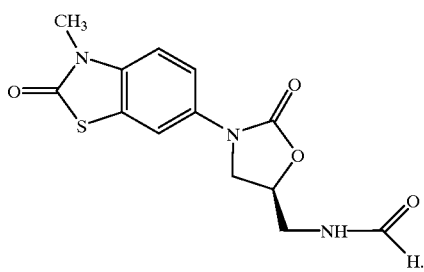

6. The compound according to claim 1, which has the formula

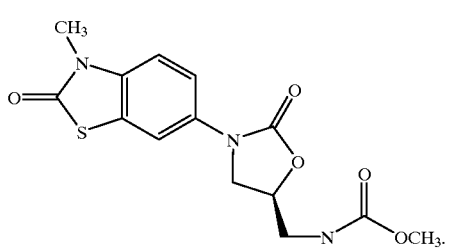

7. A antibacterial composition which comprises an effective amount of a compound according to claim 1, and an inert carrier.

8. A method of combating a bacterial infection in a host in need thereof which comprises administering an effective amount of a compond according to claim 1 and an inert carrier.

* * * * *